US008877213B2

(12) United States Patent
Nakhasi et al.

(10) Patent No.: US 8,877,213 B2
(45) Date of Patent: *Nov. 4, 2014

(54) LIVE ATTENUATED *LEISHMANIA* VACCINES

(75) Inventors: Hira L. Nakhasi, Potomac, MD (US); Angamuthu Selvapandiyan, Gaithersburg, MD (US); Alain Debrabant, Silver Spring, MD (US); Robert C. Duncan, Hyattsville, MD (US); Poonam Salotra, New Delhi (IN); Gannavaram Sreenivas, Rockville, MD (US)

(73) Assignees: The United States of America as Represented by the Secretary of the Department of Health and Human Services, Washington, DC (US); Indian Council of Medical Research, New Delhi (IN)

(*) Notice: Subject to any disclaimer, the term of this patent is extended or adjusted under 35 U.S.C. 154(b) by 539 days.

This patent is subject to a terminal disclaimer.

(21) Appl. No.: 12/946,809

(22) Filed: Nov. 15, 2010

(65) Prior Publication Data

US 2011/0081383 A1 Apr. 7, 2011

Related U.S. Application Data

(63) Continuation of application No. 11/364,682, filed on Feb. 28, 2006, now Pat. No. 7,887,812, which is a continuation of application No. PCT/US2004/028008, filed on Aug. 27, 2004.

(60) Provisional application No. 60/549,507, filed on Mar. 1, 2004, provisional application No. 60/498,816, filed on Aug. 29, 2003.

(51) Int. Cl.
| | |
|---|---|
| *A61K 39/008* | (2006.01) |
| *C12N 1/36* | (2006.01) |
| *C12N 1/10* | (2006.01) |
| *A61K 39/00* | (2006.01) |

(52) U.S. Cl.
CPC ......... *A61K 39/008* (2013.01); *A61K 2039/522* (2013.01); *C12N 1/36* (2013.01)
USPC .................................... 424/269.1; 435/258.3

(58) Field of Classification Search
None
See application file for complete search history.

(56) References Cited

U.S. PATENT DOCUMENTS

| | | | |
|---|---|---|---|
| 5,733,778 A | 3/1998 | Matlashewski et al. | |
| 6,133,017 A | 10/2000 | Matlashewski et al. | |
| 6,426,203 B1 | 7/2002 | Papadopoulou et al. | |

FOREIGN PATENT DOCUMENTS

| | | |
|---|---|---|
| CA | 2 105 538 A1 | 3/1995 |
| EP | 0 806 476 | 11/1997 |

OTHER PUBLICATIONS

Indian Council of Medical Research (ICMR) Annual Report 2002-2003 pp. 122-133.*
Baum, P. et al. "Yeast gene required for spindle pole body duplication: homology of its product with Ca2+-binding proteins" 1986, *PNAS USA* 83:5512-5516.
Burchmore, R.I.S. et al. "Genetic characterization of glucose transporter function in *Leishmania mexicana*" 2003, *PNAS USA* 100:3901-3906.
Cruz, A. et al. 1991 "Double targeted gene replacement for creating null mutants" *PNAS USA*, 88:7170-7174.
Cunningham, M.L. et al. 2001 "Regulation of differentiation to the infective stage of the protozoan parasite *Leishmania major* by tetrahydrobiopterin" 2001, *Science* 292:285-287.
Danial, N.N. et al. "Cell death: critical control points" 2004, *Cell*, 116:205-219.
Debrabant, A. et al. "Expression of cal reticulin P-domain results in impairment of secretory pathway in *Leishmania donovani* and reduced parasite survival in macrophages" 2002, *Int. J. Parasitol.* 32: 1423-1434.
Debrabant, A. et al. "Generation of *Leishmania donovani* axenic amastigotes: their growth and biological characteristics" 2004, *Intl. J. Parasitol.* 34:205-217.
Debrabant, A. et al. "Isolation and characterization of the gene encoding the surface membrane 3' -nucleotidase/nuclease of *Leishmania donovani*" 1995, *Mol. Biochem. Parasitol.* 71: 51-63.
Debrabant, A. et al. "Programmed cell death in trypanosomatids and other unicellular organisms" 2003, *Int. J. Parasitol.* 33:257-267.
Errabolu, R. et al. "Cloning of a cDNA encoding human centrin, an EF-hand protein of centrosomes and mitotic spindle poles" 1994, *J. Cell Sci.* 107:9-16.
Freedman, D.J. et al. "Two more independent selectable markers for stable transfection of *Leishmania*" 1993, *Mol. Biochem. Parasitol.* 62:37-44.
Gavet, O. et al. "Centrin4p, a novel mammalian centrin specifically expressed in ciliated cells" 2003, *Mol. Biol. Cell* 14:1818-1834.
Goyard, S. et al. 2003 "An in vitro system for developmental and genetic studies of *Leishmania donovani* phosphoglycans" *Mol. Biochem. Parasitol.* 130:31-42.
Handman, E. "Leishmaniasis: current status of vaccine development" 2001, *Clin. Microbiol. Rev.* 14:229-243.
Ilg, T. 2000 "Lipophosphoglycan is not required for infection of macrophages or mice by *Leishmania mexicana*" *EMBO J.* 19: 1953-1962.
Jiang, Y. et al. "Ornithine decarboxylase gene deletion mutants of *Leishmania donovani*" 1999, *J. Biol. Chem.* 274:3781-3788.
Joshi, P.B. et al. "Targeted gene deletion in *Leishmania major* identifies leishmanolysin (GP63) as a virulence factor" 2002, *Mol. Biochem. Parasitol.* 120:33-40.

(Continued)

*Primary Examiner* — Padma V Baskar
(74) *Attorney, Agent, or Firm* — Kilpatrick Townsend & Stockton LLP

(57) ABSTRACT

Targeted disruption of the centrin gene leads to attenuation of growth in the *Leishmania*. Preferred embodiments of the invention provide attenuated strains of *Leishmania* useful for the preparation of immunogenic preparations including vaccines against a disease caused by infection with a virulent *Leishmania* strain and as tools for the generation of immunological and diagnostic reagents. Other preferred embodiments provide related immunogenic compositions, methods of generating an immune response, methods for producing a vaccine, and methods of forming attenuated strains of *Leishmania*.

6 Claims, 15 Drawing Sheets

(56) References Cited

OTHER PUBLICATIONS

Figure 1:
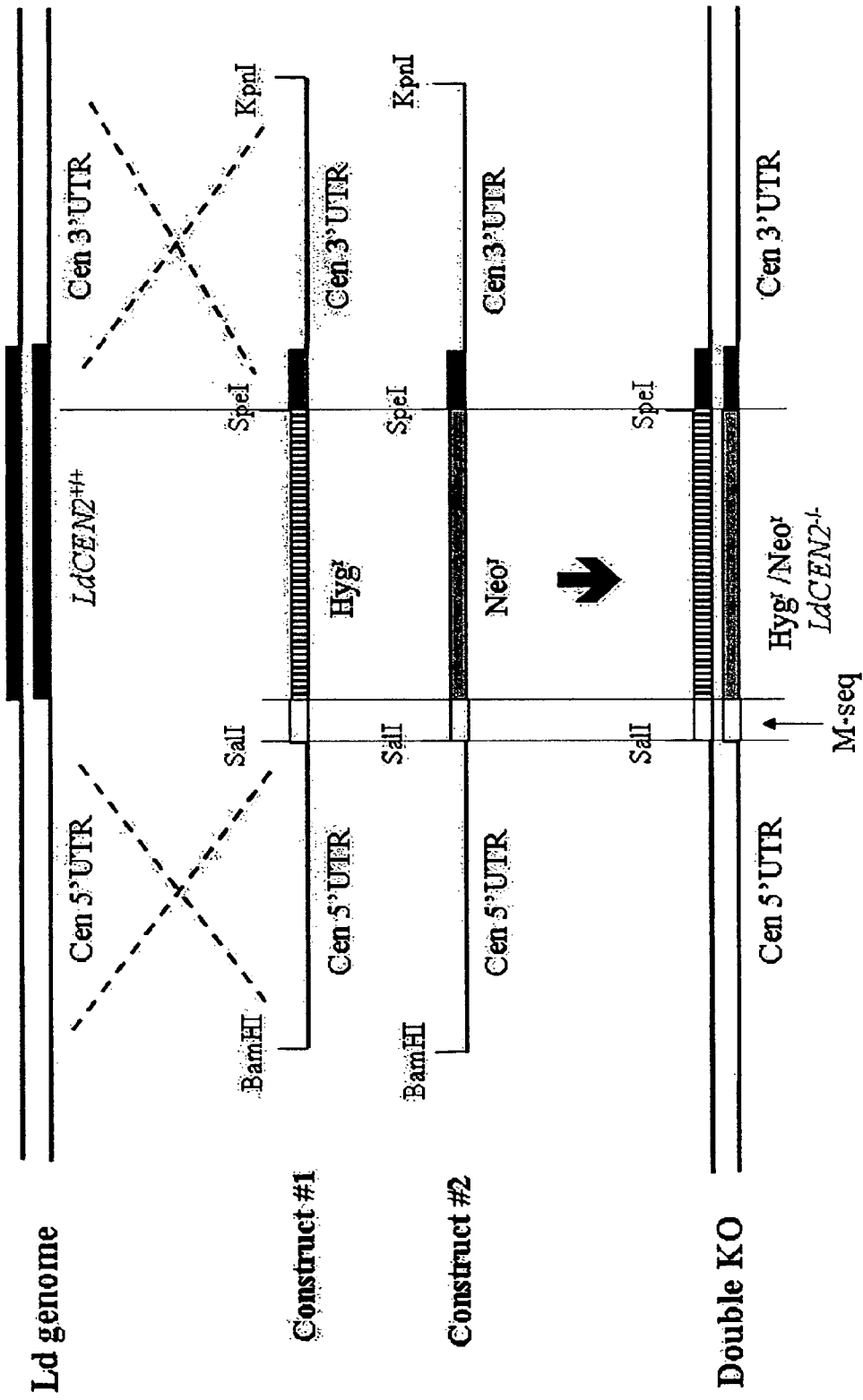

Joshi, P.B. et al. "Targeted gene deletion of *Leishmania major* genes encoding developmental stage-specific leishmanolysin (GP63)" 1998, *Mol. Microbiol.* 27:519-530.

Kilmartin, J. V. "Sfi1P has conserved centrin-binding sites and an essential function in budding yeast spindle pole body duplication" 2003, *J. Cell Biol.* 162:1211-1221.

Klink, V.P. et al. "Centrin is necessary for the formation of the motile apparatus in spermatids of mars ilea" 2001, *Mol. Biol. Cell* 12:761-776.

Koblenz, B. et al. "Centrin deficiency in *Chlamydomonas* causes defects in basal body replication, segregation and maturation" 2003, *J. Cell Sci.* 116:2635-2646.

Kokoszka, J.E. et al. "The ADP/ATP translocator is not essential for the mitochondrial permeability transition pore" 2004, *Nature* 427: 461-465.

Lee, N. et al. "Programmed cell death in the unicellular protozoan parasite *Leishmania*" 2002, *Cell Death Differ.* 9:53-64.

Lingle, W.L. et al. "Centrosome hypertrophy in human breast tumors: Implications for genomic stability and cell polarity" 1998, *PNAS USA* 95:2950-2955.

Ogbadoyi, E.O. et al. "A high-order trans-membrane structural linkage is responsible for mitochondrial genome positioning and segregation by flagellar basal bodies in trypanosomes" 2003, *Mol. Biol. Cell* 14: 1769-1779.

Paoletti, A. et al. "Fission yeast cdc31p is a component of the half-bridge and controls SPB duplication" 2003, *Mol. Biol. Cell* 14:2793-2808.

Piel, M. et al. "Centrosome-dependent exit of cytokinesis in animal cells" 2001, *Science* 291: 1550-1553.

Roberts, S.C. et al. "Genetic analysis of spermidine synthase from *Leishmania donovani*" 2001, *Mol. Biochern. Parasitol.* 115:217-226.

Robinson, D.R. et al. "Basal body movements as a mechanism for mitochondrial genome segregation in the trypanosome cell cycle." 1991, *Nature* 352:731-733.

Salisbury, J.L. "Centrin, centrosomes, and mitotic spindle poles" 1995, *Curr. Opin. Cell Biol.* 7:39-45.

Salisbury, J.L. "Centrosomes: coiled-coils organize the cell center" 2003, *Curr. Biol.* 13:R88-R90.

Salisbury, J.L. "Centrosomes: Sfilp and centrin unravel a structural riddle." 2004, *Curr. Biol.* 14:R27-R29.

Salisbury, J.L. et al. "Centrin-2 is required for centriole duplication in mammalian cells" 2002, *Curr. Biol.* 12: 1287-1292.

Selvapandiyan, A. et al. "Centrin gene disruption impairs stage-specific basal body duplication and cell cycle progression in *Leishmania*" 2004, *J. Biol. Chem.* 279:25703-25710.

Selvapandiyan, A. et al. "Expression of a mutant form of *Leishmania donovani* centrin reduces the growth of the parasite" 2001, *J. Biol. Chem.*. 276:43253-43261.

Spath, G.F. et al. "Lipophosphoglycan is a virulence. factor distinct from related glycoconjugates in the protozoan parasite *Leishmania major*" 2000, *PNAS USA* 97:9258-9263.

Spath, G.F. et al. "The role(s) of lipophosphoglycan (LPG) in the establishment of *Leishmania major* infections in mammalian hosts" 2003, *PNAS USA* 100:9536-9541.

Sreenivas, G. et al. "Arbitrary-primed per for genomic fingerprinting and identification of differentially regulated genes in indian isolates of *Leishmania donovani*" 2004, *Exp. Parasitol.* 106: 110-118.

Titus, R.G. et al. "Development of a safe live *Leishmania* vaccine line by gene replacement" 1995, *PNAS USA* 92:10267-10271.

Vallen, E.A. et al. "Genetic interactions between CDC31 and KAR1, two genes required for duplication of the microtubule organizing center in *Saccharomyces cerevisiae*" 1994, *Genetics* 137:407-422.

Zhang, W.W. et al. "Identification and overexpression of the A2 amastigote-specific protein in *Leishmania donovani*" 1996, *Mol. Biochem. Parasitol.* 78:79-90.

* cited by examiner

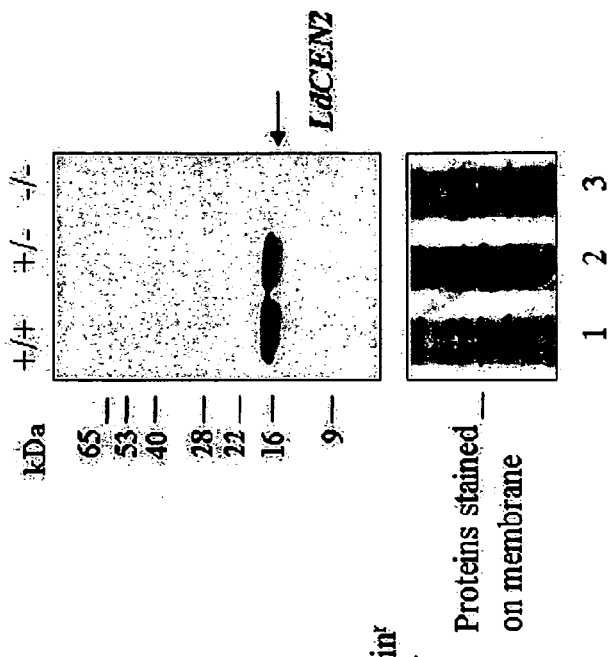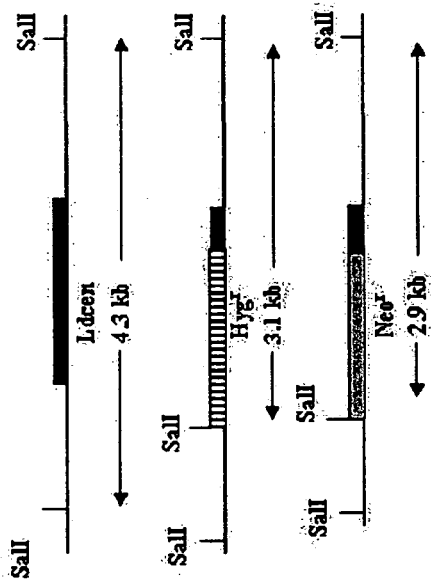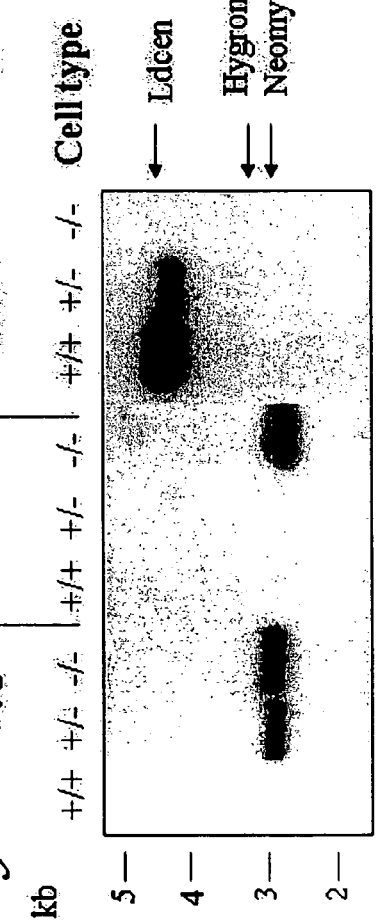

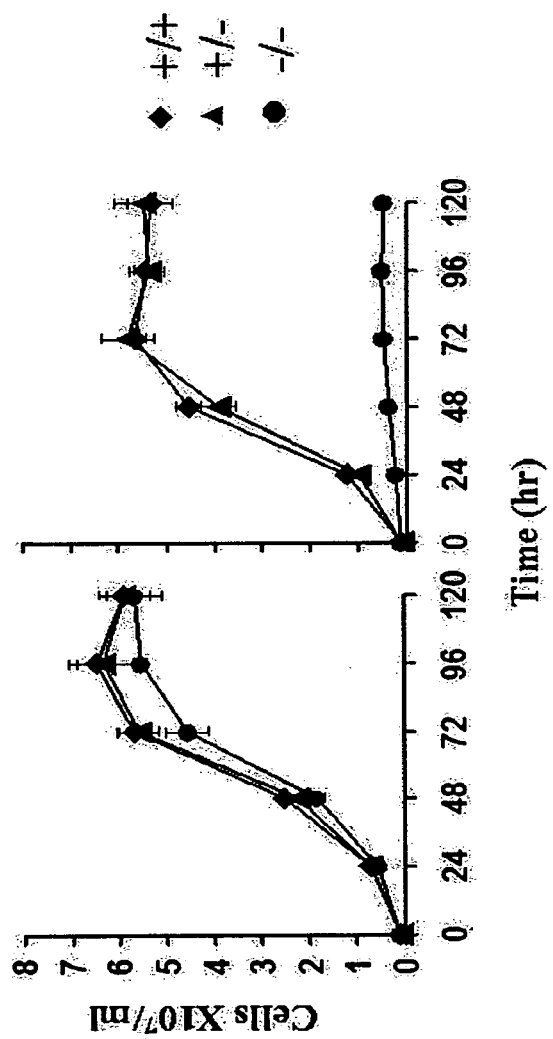

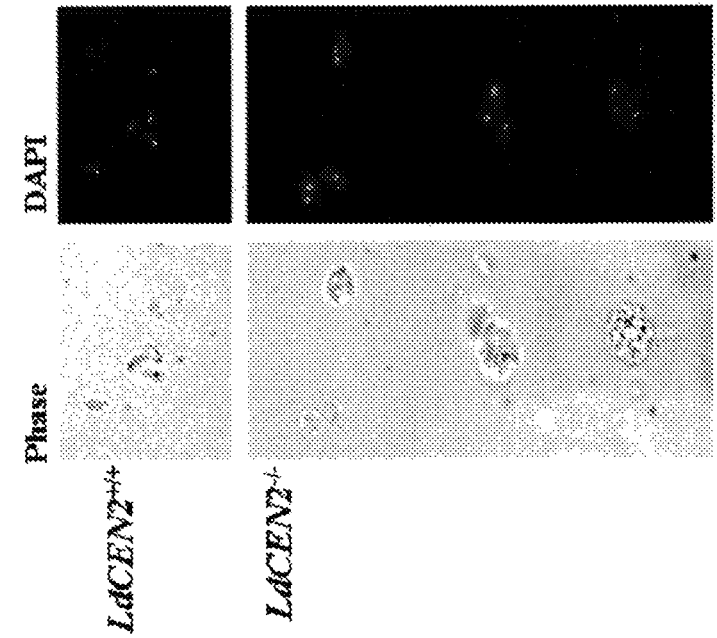
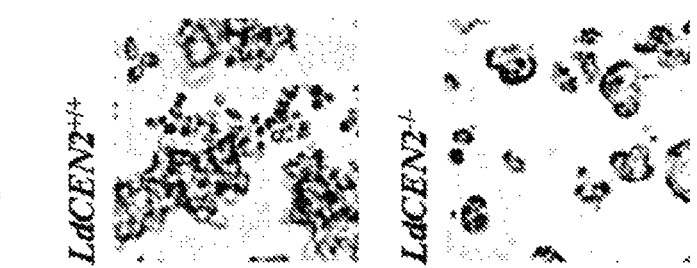
FIG. 7A
FIG. 7B

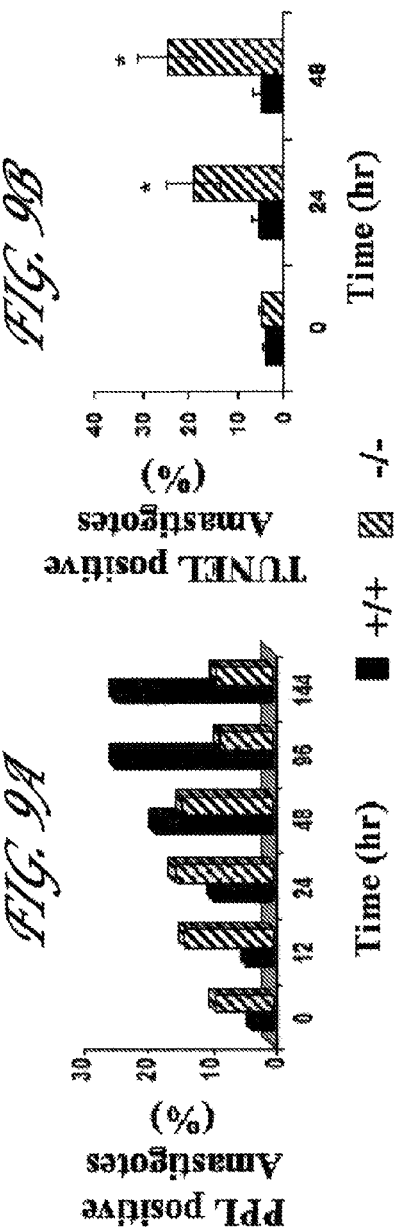
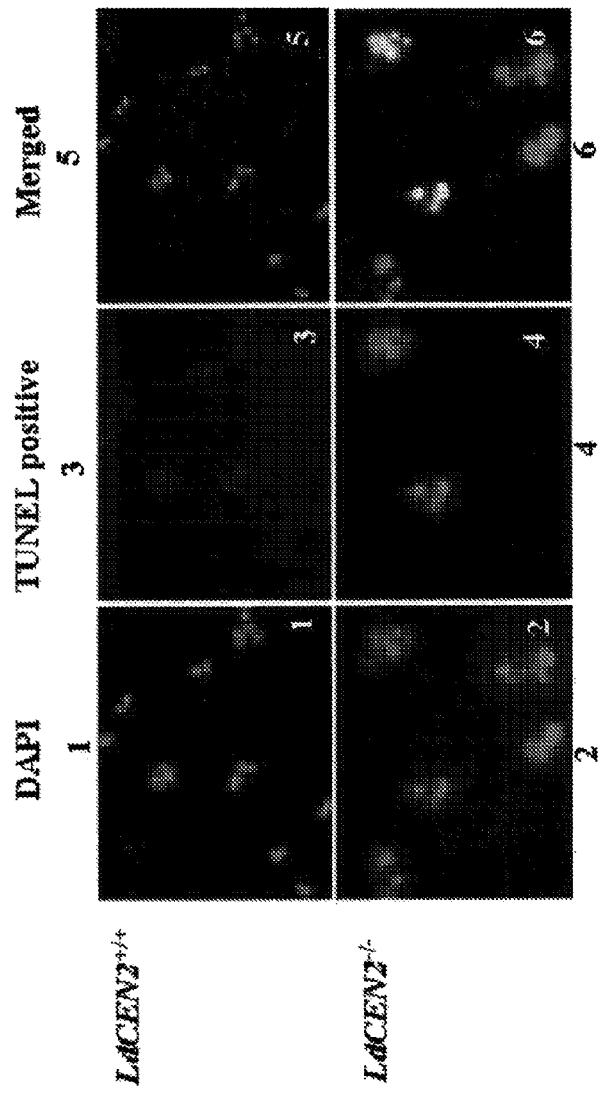

*Leishmania donovani* centrin (centrin that has been deleted in *L. donovani*) (SEQ ID NO:1)

ATGGCTGCGCTGACGGATGAACAGATTCGCGAGGCCTTCAACCTCTTCGA
CGCCGACGGCTCTGGCGCTATCGACGCGGAGGAGATGGCGCTAGCGATGA
AGGGTCTCGGGTTCGGTGACCTGTCGCGCGACGAGGTGGAGCGCATTATC
CGCTCTATGCACACAGACTCGAACGGTCTGGTGGCGTACGGCGAGTTTGA
GGCCATGGTCAAGTCGCGCATGGCGCAGAAGGACTCGCCGGAGGAGATC
CTAAAGGCCTTTCAGCTCTTCGACCTCGATAAGAAAGGCAAAATCTCCTTT
GCGAACTTGAAGGAGGTTGCGAAACTGCTGGGTGAGAACCCCGGCGACG
ATGTGCTGAAGGAGATGATCGCCGAGGCCGATGAGGACGGTGATGGCGA
GGTGTCCTTCGAGGAGTTCAAGAGCGTGATGCTGCAGATGCGTGGAAAG

Sequences of centrins identical to *L. donovani* centrin found in other species are:

*Leishmania infantum* centrin (SEQ ID NO: 2)

ATGGCTGCGCTGACGGATGAACAGATTCGCGAGGCCTTCAACCTCTTCGA
CGCCGACGGCTCTGGCGCTATCGACGCGGAGGAGATGGCGCTAGCGATGA
AGGGTCTCGGGTTCGGTGACCTGTCGCGCGACGAGGTGGAGCGCATTATC
CGCTCTATGCACACAGACTCGAACGGTCTGGTGGCGTACGGCGAGTTTGA
GGCCATGGTCAAGTCGCGCATGGCGCAGAAGGACTCGCCGGAGGAGATC
CTAAAGGCCTTTCAGCTCTTCGACCTCGATAAGAAAGGCAAAATCTCCTTT
GCGAACTTGAAGGAGGTTGCGAAACTGCTGGGTGAGAACCCCGGCGACG
ATGTGCTGAAGGAGATGATCGCCGAGGCCGATGAGGACGGTGATGGCGA
GGTGTCCTTCGAGGAGTTCAAGAGCGTGATGCTGCAGATGCGTGGAAAG

*Leishmania amazonensis* centrin (SEQ ID NO: 3)

ATGGCTGCGCTGACGGATGAACAGATTCGCGAGGCCTTCAACCTCTTTGA
CGCCGACGGCTCTGGCGCTATCGACGCGGAGGAGATGGCGCTAGCGATGA
AGGGTCTCGGCTTCGGTGACCTGTCGCGCGACGAGGTGGAGCGCATCATC
CGCTCCATGCACACGGACTCCAACGGCCTGGTGGCGTACGGTGAGTTTGA
GGCCATGGTCAAGTCACGCATGGCGCAGAAGGACTCGCCGGAGGAGATC
CTAAAGGCCTTTCAGCTCTTCGACCTCGATAAGAAGGGAAAATTTCGTTT
GCGAACTTGAAGGAAGTGGCGAAACTGCTGGGTGAGAACCCCGGCGACG
ATGTGCTGAAGGAGATGATCGCCGAGGCCGATGAGGACGGTGATGGCGA
GGTGTCCTTTGAGGAGTTCAAGAGCGTGATGCTGCAGATGCGTGGAAAG

*FIG. 12A*

*Leishmania major* centrin (SEQ ID NO: 4)

ATGGCTGCGCTGACGGATGAGCAGATTCGCGAGGCCTTCAACCTCTTCGA
CGCCGACGGCTCTGGGGCTATCGACGCGGAGGAGATGGCGCTAGCGATGA
AGGGTCTCGGCTTCGGTGACCTGTCGCGCGACGAGGTGGAGCGCATTATC
CGCTCCATGCACACAGACTCCAACGGCCTGGTGGCGTACGGCGAGTTTGA
AGCCATGGTCAAGTCGCGCATGGCGCAGAAGGACTCGCCGGAGGAGATC
CTAAAGGCCTTTCAGCTCTTCGACCTCGATAAGAAAGGAAAAATCTCCTTT
GCGAACTTGAAGGAGGTTGCGAAACTGCTGGGTGAGAACCCCGGCGACG
ATGTGCTGAAGGAGATGATTGCCGAGGCCGATGAGGACGGTGATGGCGA
GGTTTCCTTTGAGGAGTTCAAGAGCGTGATGCTGCAGATGCGTGGAAAG

*Leishmania mexicana* centrin (SEQ ID NO: 5)

ATGGCTGCGCTGACGGATGAACAGATTCGCGAGGCCTTCAACCTCTTTGA
CGCCGACGGCTCTGGCGCTATCGACGCGGAGGAGATGGCGCTAGCGATGA
AGGGTCTCGGCTTCGGTGACCTGTCGCGCGACGAGGTGGAGCGCATCATC
CGCTCCATGCACACGGACTCCAACGGCCTGGTGGCGTACGGCGAGTTTGA
GGCCATGGTCAAGTCGCGCATGGCGCAGAAGGACTCGCCGGAGGAGATC
CTAAAGGCCTTTCAGCTCTTCGACCTCGATAAGAAAGGGAAAATTTCGTTT
GCGAACTTGAAGGAGGTGGCGAAACTGCTGGGTGAGAACCCCGGCGACG
ATGTGCTGAAGGAGATGATCGCCGAGGCCGATGAGGACGGTGATGGCGA
GGTGTCCTTTGAGGAGTTCAAGAGCGTGATGCTGCAGATGCGTGGAAAG

*Leishmania tropica* centrin (SEQ ID NO: 6)

ATGGCTGCGCTGACGGATGAGCAGATTCGCGAGGCCTTCAACCTCTTCGA
CGCCGACGGCTCTGGCGCTATCGACGCGGAGGAGATGGCGCTAGCGATGA
AGGGTCTCGGCTTCGGTGACCTGTCGCGCGACGAGGTGGAGCGCATTATC
CGCTCCATGCACACAGACTCCAACGGCCTGGTGGCGTACGGCGAGTTTGA
GGCCATGATCAAGTCGCGCATGGCGCAGAAGGACTCGCCGGAGGAGATC
CTAAAGGCCATTCAGCTCTTCGACCTCGATAAGAAAGGAAAAATCTCCTT
TGCGAACTTGAAGGAGGTTGCGAAACTGCTGGGTGAGAACCCCGGCGACG
ATGTGCTGAAGGAGATGATCGCCGAGGCCGATGAGGACGGTGATGGCGA
GGTTTCCTTTGAGGAGTTCAAGAGCGTGATGCTGCAGATGCGTGGAAAG

FIG. 12B

SEQUENCE LISTING

```
<160> NUMBER OF SEQ ID NOS: 16

<210> SEQ ID NO 1
<211> LENGTH: 447
<212> TYPE: DNA
<213> ORGANISM: Leishmania donovani

<400> SEQUENCE: 1
atggctgcgc tgacggatga acagattcgc gaggccttca acctcttcga cgccgacggc      60
tctggcgcta tcgacgcgga ggagatggcg ctagcgatga agggtctcgg gttcggtgac     120
ctgtcgcgcg acgaggtgga gcgcattatc cgctctatgc acacagactc gaacggtctg     180
gtggcgtacg gcgagtttga ggccatggtc aagtcgcgca tggcgcagaa ggactcgccg     240
gaggagatcc taaaggcctt tcagctcttc gacctcgata agaaaggcaa aatctccttt     300
gcgaacttga aggaggttgc gaaactgctg ggtgagaacc ccggcgacga tgtgctgaag     360
gagatgatcg ccgaggccga tgaggacggt gatggcgagg tgtccttcga ggagttcaag     420
agcgtgatgc tgcagatgcg tggaaag                                         447

<210> SEQ ID NO 2
<211> LENGTH: 447
<212> TYPE: DNA
<213> ORGANISM: Leishmania infantum

<400> SEQUENCE: 2
atggctgcgc tgacggatga acagattcgc gaggccttca acctcttcga cgccgacggc      60
tctggcgcta tcgacgcgga ggagatggcg ctagcgatga agggtctcgg gttcggtgac     120
ctgtcgcgcg acgaggtgga gcgcattatc cgctctatgc acacagactc gaacggtctg     180
gtggcgtacg gcgagtttga ggccatggtc aagtcgcgca tggcgcagaa ggactcgccg     240
gaggagatcc taaaggcctt tcagctcttc gacctcgata agaaaggcaa aatctccttt     300
gcgaacttga aggaggttgc gaaactgctg ggtgagaacc ccggcgacga tgtgctgaag     360
gagatgatcg ccgaggccga tgaggacggt gatggcgagg tgtccttcga ggagttcaag     420
agcgtgatgc tgcagatgcg tggaaag                                         447

<210> SEQ ID NO 3
<211> LENGTH: 447
<212> TYPE: DNA
<213> ORGANISM: Leishmania amazonensis

<400> SEQUENCE: 3
atggctgcgc tgacggatga acagattcgc gaggccttca acctctttga cgccgacggc      60
tctggcgcta tcgacgcgga ggagatggcg ctagcgatga agggtctcgg cttcggtgac     120
ctgtcgcgcg acgaggtgga gcgcatcatc cgctccatgc acacggactc caacggcctg     180
gtggcgtacg gtgagtttga ggccatggtc aagtcacgca tggcgcagaa ggactcgccg     240
gaggagatcc taaaggcctt tcagctcttc gacctcgata agaaagggaa aatttcgttt     300
gcgaacttga aggaagtggc gaaactgctg ggtgagaacc ccggcgacga tgtgctgaag     360
```

```
gagatgatcg ccgaggccga tgaggacggt gatggcgagg tgtcctttga ggagttcaag      420
agcgtgatgc tgcagatgcg tggaaag                                          447

<210> SEQ ID NO 4
<211> LENGTH: 447
<212> TYPE: DNA
<213> ORGANISM: Leishmania major

<400> SEQUENCE: 4
atggctgcgc tgacggatga gcagattcgc gaggccttca acctcttcga cgccgacggc      60
tctggggcta tcgacgcgga ggagatggcg ctagcgatga agggtctcgg cttcggtgac     120
ctgtcgcgcg acgaggtgga gcgcattatc cgctccatgc acacagactc caacggcctg     180
gtggcgtacg gcgagtttga agccatggtc aagtcgcgca tggcgcagaa ggactcgccg     240
gaggagatcc taaaggcctt tcagctcttc gacctcgata agaaaggaaa aatctccttt     300
gcgaacttga aggaggttgc gaaactgctg ggtgagaacc ccggcgacga tgtgctgaag     360
gagatgattg ccgaggccga tgaggacggt gatggcgagg tttcctttga ggagttcaag     420
agcgtgatgc tgcagatgcg tggaaag                                          447

<210> SEQ ID NO 5
<211> LENGTH: 447
<212> TYPE: DNA
<213> ORGANISM: Leishmania mexicana

<400> SEQUENCE: 5
atggctgcgc tgacggatga acagattcgc gaggccttca acctctttga cgccgacggc      60
tctggcgcta tcgacgcgga ggagatggcg ctagcgatga agggtctcgg cttcggtgac     120
ctgtcgcgcg acgaggtgga gcgcatcatc cgctccatgc acacggactc caacggcctg     180
gtggcgtacg gcgagtttga ggccatggtc aagtcgcgca tggcgcagaa ggactcgccg     240
gaggagatcc taaaggcctt tcagctcttc gacctcgata agaaagggaa atttcgtttt     300
gcgaacttga aggaggtggc gaaactgctg ggtgagaacc ccggcgacga tgtgctgaag     360
gagatgatcg ccgaggccga tgaggacggt gatggcgagg tgtcctttga ggagttcaag     420
agcgtgatgc tgcagatgcg tggaaag                                          447

<210> SEQ ID NO 6
<211> LENGTH: 447
<212> TYPE: DNA
<213> ORGANISM: Leishmania tropica

<400> SEQUENCE: 6
atggctgcgc tgacggatga gcagattcgc gaggccttca acctcttcga cgccgacggc      60
tctggcgcta tcgacgcgga ggagatggcg ctagcgatga agggtctcgg cttcggtgac     120
ctgtcgcgcg acgaggtgga gcgcattatc cgctccatgc acacagactc caacggcctg     180
gtggcgtacg gcgagtttga ggccatgatc aagtcgcgca tggcgcagaa ggactcgccg     240
gaggagatcc taaaggccat tcagctcttc gacctcgata agaaaggaaa aatctccttt     300
gcgaacttga aggaggttgc gaaactgctg ggtgagaacc ccggcgacga tgtgctgaag     360
gagatgatcg ccgaggccga tgaggacggt gatggcgagg tttcctttga ggagttcaag     420
agcgtgatgc tgcagatgcg tggaaag                                          447

<210> SEQ ID NO 7
```

```
<211> LENGTH: 22
<212> TYPE: DNA
<213> ORGANISM: Artificial Sequence
<220> FEATURE:
<223> OTHER INFORMATION: synthetic primer P1

<400> SEQUENCE: 7
gggatcctta tagccacgga tg                                            22

<210> SEQ ID NO 8
<211> LENGTH: 24
<212> TYPE: DNA
<213> ORGANISM: Artificial Sequence
<220> FEATURE:
<223> OTHER INFORMATION: synthetic primer P2

<400> SEQUENCE: 8
gggtcgaccc acaaaaagaa attg                                          24

<210> SEQ ID NO 9
<211> LENGTH: 24
<212> TYPE: DNA
<213> ORGANISM: Artificial Sequence
<220> FEATURE:
<223> OTHER INFORMATION: synthetic primer P3

<400> SEQUENCE: 9
gactagtact gctgggtgag aacc                                          24

<210> SEQ ID NO 10
<211> LENGTH: 25
<212> TYPE: DNA
<213> ORGANISM: Artificial Sequence
<220> FEATURE:
<223> OTHER INFORMATION: synthetic primer P4

<400> SEQUENCE: 10
gggtacctat ttatcgcctg ctcgg                                         25

<210> SEQ ID NO 11
<211> LENGTH: 52
<212> TYPE: DNA
<213> ORGANISM: Artificial Sequence
<220> FEATURE:
<223> OTHER INFORMATION: synthetic primer P5

<400> SEQUENCE: 11
ggtcgacgct acggcagaca tggctcgagc tctgatgaaa aagcctgaac tc           52

<210> SEQ ID NO 12
<211> LENGTH: 25
<212> TYPE: DNA
<213> ORGANISM: Artificial Sequence
<220> FEATURE:
<223> OTHER INFORMATION: synthetic primer P6

<400> SEQUENCE: 12
ggactagtct attcctttgc cctcg                                         25

<210> SEQ ID NO 13
<211> LENGTH: 52
<212> TYPE: DNA
<213> ORGANISM: Artificial Sequence
<220> FEATURE:
<223> OTHER INFORMATION: synthetic primer P7

<400> SEQUENCE: 13
```

```
ggtcgacgct acggcagaca tggctcgagc tctgatgatt gaacaagatg ga        52

<210> SEQ ID NO 14
<211> LENGTH: 24
<212> TYPE: DNA
<213> ORGANISM: Artificial Sequence
<220> FEATURE:
<223> OTHER INFORMATION: synthetic primer P8

<400> SEQUENCE: 14
gactagtcag aagaactcgt caag                                       24

<210> SEQ ID NO 15
<211> LENGTH: 25
<212> TYPE: DNA
<213> ORGANISM: Artificial Sequence
<220> FEATURE:
<223> OTHER INFORMATION: synthetic primer P9

<400> SEQUENCE: 15
gggatccatg gctgcgctga cggat                                      25

<210> SEQ ID NO 16
<211> LENGTH: 55
<212> TYPE: DNA
<213> ORGANISM: Artificial Sequence
<220> FEATURE:
<223> OTHER INFORMATION: synthetic primer P10

<400> SEQUENCE: 16 gggatccta cgcgtagtcc ggcacgtcgt acgggtactt tccacgcatg tgcag      55
```

LIVE ATTENUATED *LEISHMANIA* VACCINES

CROSS-REFERENCES TO RELATED APPLICATIONS

The present application is a continuation application of U.S. patent application Ser. No. 11/364,682, filed Feb. 28, 2006, which is a continuation of International Patent Application No. PCT/US2004/028008, filed Aug. 27, 2004, designating the U.S. and published in English on Mar. 10, 2005 as WO 2005/021030, which claims the benefit of U.S. Provisional Application No. 60/498,816, filed Aug. 29, 2003, and U.S. Provisional Application No. 60/549,507, filed Mar. 1, 2004, all of which are hereby incorporated by reference in their entireties.

FIELD OF THE INVENTION

Targeted disruption of the centrin gene leads to attenuation of growth in *Leishmania*.

BACKGROUND OF THE INVENTION

Vector borne disease, Leishmaniasis currently threatens 1.5-2.0 million people annually with an estimated death toll of 50,000 persons/year in 88 countries around the world (Ganguly, N. K. 2002 Special Program for Research and Training in Tropical Diseases News. Geneva: United Nations Development Programme/World Bank/World Health Organizations, Report no. 68; Singh, N. et al. 2003 *J Infect Dis* 188: 600-607). The parasitic disease has a wide range of clinical symptoms, which include the cutaneous form caused by *Leishmania aethiopica*, *L. mexicana*, *L. major* and *L. tropica*, the mucocutaneous form by *L. braziliensis* and the visceral form by *L. chagasi*, *L. donovani* and *L. infantum*, which is fatal if not treated in the case of *L. donovani*. Vector control is difficult and complicated by the diverse ecology of many species of sand fly vectors and animal reservoirs (Sharifi, I. et al. 1998 *Lancet* 351:1540-1543). Treatment for these diseases involves chemotherapy using antimony-based drugs, which is less effective in immunocompromised individuals (Handman, E. 2001 *Clin Microbiol Rev* 14:229-243). No effective vaccine is yet available for any of these diseases.

SEGUE TO THE INVENTION

The parasite has a digenic life style with one form called the promastigote that resides extracellularly in the mid-gut of the sand-fly vector and the other the amastigote form that multiplies intra-cellularly in the vertebrate macrophages. These two forms have been adapted to grow under in vitro conditions (Debrabant, A. et al. 2003 *Int J Parasitol* 33:257-267; Goyard, S. et al. 2003 *Mol Biochem Parasitol* 130:31-42; Joshi, M. et al. 1993 *Mol Biochem Parasitol* 58:345-354). Defects in growth have been correlated with the attenuation of virulence in *Leishmania* (Denise, H. et al. 2003 *Infect Immun* 71:3190-3195; Handman, E. 2001 *Clin Microbiol Rev* 14:229-243). In order to develop an avirulent *Leishmania* deficient for growth in vertebrate macrophages we generated a gene-targeted deletion for a key growth regulating gene, *L. donovani* centrin (LdCEN) (Selvapandiyan, A. et al. 2001 *J Biol Chem* 276:43253-43261). The centrins are basal body associated calcium binding proteins. Centrin has been characterized in other eukaryotes from unicellular *Chlamydomonas* (Koblenz, B. et al. 2003 *J Cell Sci* 116:2635-2646; Salisbury, J. L. 1995 *Curr Opin Cell Biol* 7:39-45) to humans (Errabolu, R. et al. 1994 *J Cell Sci* 107:9-16; Gavet, O. et al.

2003 *Mol Biol Cell* 14:1818-1834; Matei, E. et al. 2003 *Biochemistry* 42:1439-1450; Salisbury, J. L. et al. 2002 *Curr Biol,* 12: 1287-1292). Fibers composed of the centrin-binding protein Sfi1p and centrin act as contractile or elastic connections between centrioles/basal bodies and other elements of the centrosome to mediate dynamic changes in its overall structure (Kilmartin, J. V. 2003 *J Cell Biol* 162:1211-1221; Salisbury, J. L. 2004 *Curr Biol* 14:R27-29). Protein sequence similarity and immunoreactivity confirmed that *Leishmania* centrin is a homolog of human centrin 2 (Selvapandiyan, A. et al. 2001 *J Biol. Chem.* 276:43253-43261). LdCen-p protein is highly expressed in rapidly growing parasites of both forms and declines when cells reach stationary phase (Selvapandiyan, A. et al. 2001 *J Biol. Chem.* 276:43253-43261). Expression of N-terminal deleted centrin in the parasite significantly reduces the growth rate of both the stages of the parasite (Selvapandiyan, A. et al. 2001 *J Biol Chem.* 276: 43253-43261). These studies indicate that centrin has an important functional role in *Leishmania* growth. Many earlier studies have also elucidated the importance of the centrin gene in various cell processes, for example, conditional mutations in yeast centrin (CDC31) resulted in failure of duplication of the spindle pole body (yeast centrosome) and arrest in mitosis (Baum, P. et al. 1986 *PNAS USA.* 83:5512-5516; Paoletti, A. 2003 *Mol Biol Cell* 14:2793-2808). Silencing the centrin gene in the water fern *Marsilea vestita* effectively inhibits the formation of motile cells (Klink, V. P. and Wolniak, S. M. 2001 *Mol Biol Cell* 12:761-776). Silencing of human centrin 2 in HeLa cells impaired centriole duplication and result in failure of cytokinesis (Salisbury, J. L. et al. 2002 *Curr Biol.* 12: 1287-1292). A centrin deficient mutant of *Chlamydomonas* was non-flagellate due to defects in the flagellar root system (Koblenz, B. et al. 2003 *J Cell Sci* 116:2635-2646). Abnormal centrosomes were noticed in human tumor cells due to the presence of excess levels of many centrosome proteins including centrin (Lingle, W. L. et al. 1998 *PNAS USA* 95:2950-2955; Lingle, W. L. and Salisbury, J. L. 1999 *Am J Pathol* 155:1941-1951). In order to further analyze the characteristics of centrin in the important human parasite, *L. donovani*, we targeted LdCEN gene for a null mutation.

Various types of *Leishmania* vaccine strategies have been attempted with little success. Attenuated parasitic strains obtained through γ-irradiation, long-term in vitro culture, selection for temperature sensitivity, or chemical mutagenesis, possess genetically undefined mutations (Handman, E. 2001 *Clin Microbiol Rev* 14:229-243). Such parasites can revert back to the virulent form or persist for long periods of time. Persistence of asymptomatic *Leishmania* infections raises the risk of subsequent reactivation, especially in AIDS where leishmaniasis is an opportunistic infection (Titus, R. G. et al. 1995 *PNAS USA* 92:10267-10271). An alternate promising strategy is to generate nonreversible genetically defined attenuated parasites by deleting known essential genes. To date, few genetically defined mutations have been carried out in *Leishmania*. Dihydrofolate reductase-thymidylate synthase and Leishmanolysin genes were deleted in *L. major* (Cruz, A. et al. 1991 *PNAS USA* 88:7170-7174; Joshi, P. B. et al. 2002 *Mol Biochem Parasitol* 120:33-40; Joshi, P. B. et al. 1998 *Mol Microbiol* 27:519-530; Titus, R. G. et al. 1995 *PNAS USA* 92:10267-10271) and genes involved in Lipophosphoglycan were deleted in *L. mexicana* and *L. major* (Ilg, T. 2000 *Embo J* 19:1953-1962; Spath, G. F. et al. 2000 *PNAS USA* 97:9258-9263; Spath, G. F. et al. 2003 *PNAS USA* 100: 9536-41). While the outcome of vaccine efficacy testing of these mutant *L. major/mexicana* strains is being evaluated, we envision the generation of a nonreversible genetically defined attenuated vaccine for *L. donovani* based on the outcome of the studies on centrin gene deletion.

Studying the characteristics of genes and generating mutant organisms through silencing the corresponding mRNA to translate into proteins, via RNA interference (RNAi) approach, is successful in many eukaryotes including the parasites *T. brucei* (Wang, Z. et al. 2000 *J Biol Chem* 275: 40174-40179) and *Plasmodium falciparum* (Malhotra, P. et al. 2002 *Mol Microbiol* 45:1245-1254). This approach has so far been unsuccessful in *Leishmania* probably due to lack of RNAi processing machinery in these organisms (Robinson, K. A. and Beverley, S. M. 2003 *Mol Biochem Parasitol* 128: 217-228). However, gene replacement through homologous recombination is still a powerful method for altering and testing gene function (Capecchi, M. R. 1989 *Science* 244: 1288-1292; Cruz, A. et al. 1991 *PNAS USA* 88:7170-7174). Unlike many other eukaryotes, *Leishmania* is diploid throughout its life cycle. Hence it may be necessary to delete both the alleles of a gene such as by targeting with two different marker genes (Cruz, A. et al. 1991 *PNAS USA* 88:7170-7174). In this disclosure we describe a stepwise disruption of the two alleles of LdCEN, using genes resistant to antibiotics hygromycin B and G418 (Geneticin) and characterization of the LdCEN null mutant parasites for their growth both extracellularly as promastigotes as well as axenic amastigotes and inside macrophages. The purpose of the disclosure is to establish correlation between centrin expression and parasite growth and characterize the LdCEN null mutants for use as a live attenuated vaccine.

SUMMARY OF THE INVENTION

Targeted disruption of the centrin gene leads to attenuation of growth in *Leishmania*. Preferred embodiments of the invention provide attenuated strains of *Leishmania* useful for the preparation of immunogenic preparations including vaccines against a disease caused by infection with a virulent *Leishmania* strain and as tools for the generation of immunological and diagnostic reagents. Other preferred embodiments provide related immunogenic compositions, methods of generating an immune response, methods for producing a vaccine, and methods of forming attenuated strains of *Leishmania*.

BRIEF DESCRIPTION OF THE DRAWINGS

FIG. 1 Schematic diagram showing design and use of constructs for LdCEN gene disruption in the *L. donovani* genome. Constructs 1 and 2 show hyg or neo genes respectively, flanked on the 5' and 3' sides with LdCEN 5'UTR and 3'UTR respectively. The lengths of the antibiotic resistant genes and the LdCEN untranslated regions have been described in Example 1. M-seq: 14 nucleotides upstream and 12 nucleotides downstream of the ATG start codon of 3'NT/Nu gene. BamHI, KpnI, SalI and SpeI are the restriction sites.

FIG. 2 (A) Schematic drawing of the centrin locus in *L. donovani* with SalI restriction sites. Disrupting the centrin gene with either hyg or neo gene generates an additional SalI site at the 5' end of the selectable marker genes. (B) Southern blot analysis of the genomic DNA of *Leishmania* wild type (+/+), LdCEN single (+/−) and double (−/−) allele disrupted parasites with hyg, neo and LdCEN genes as $^{32}P$ labeled probes. The genomic DNA from the parasites was cut with the restriction enzyme SalI and used in the analysis. (C) Western blot analysis of the lysates of +/+, +/− and −/− parasites using αLdCen Ab (Selvapandiyan, A. et al. 2001 *J Biol Chem,* 276:43253-43261). Lower panel: After the protein transfer the membrane was stained with Ponceau S to control for protein loading.

FIG. 3 The effect of LdCEN disruption on the growth of in vitro grown *Leishmania* promastigotes (A) and axenic amastigotes (B) of wild type (+/+), centrin single allele disrupted (+/−) and centrin both the alleles disrupted (−/−). The cells were grown in the absence of antibiotics. Initial cell density in the culture was $0.1\times10^7$ cells/ml. Data represent the mean±SD of four independent experiments.

FIG. 4 Indirect immunofluorescence analysis of centrin distribution in (A) wild type promastigote and (B) amastigote, and (C) LdCEN$^{-/-}$ promastigote and (D) amastigote cells. Centrin staining at the flagellar base and along the axoneme is evident in promastigote cells and at the flagellar basal apparatus in wild type amastigote cells. LdCEN$^{-/-}$ amastigote cells are largely devoid of specific staining. Bar=5 μm.

FIG. 5 Electron microscopy of the flagellar apparatus of (A) wild type promastigote and (B) amastigote, and (C) LdCEN$^{-/-}$ promastigote and (D) amastigote cells. Evidence of duplication with more than two basal bodies was frequently observed in (E) wild type promastigote and (F) amastigote, and (G) LdCEN$^{-/-}$ promastigote cells, but not in (H) amastigote cells where more than two basal bodies were never seen. Bar=0.5 μm.

FIG. 6 Flow cytometric analysis of the DNA content of *L. donovani* wild type (+/+) and centrin deficient (−/−) parasites. Promastigotes inoculated at $1\times10^6$ cells/ml in axenic amastigote medium were allowed to grow 24 or 48 hr. The resulting axenic amastigotes were harvested, fixed, stained with propidium iodide and subjected to fluorescence-activated cell scan analysis. The percent of cells in each cell cycle stage, G1, S or G2/M, is plotted for the 24 hr time point (bar graph to the left) and 48 hr time point (bar graph to the right). Solid bars indicate the wild type cells (+/+) and hatched bars indicate the centrin deficient (−/−) cells. Data represent the mean±SD of three independent experiments. $^*P<0.008$ and $^{**}P<0.0005$ student's t-test.

FIG. 7 (A) Phase contrast images of *L. donovani* wild type (+/+) and centrin deficient (−/−) axenic amastigotes after 48 hr of in vitro culture. (B) Para-formaldehyde fixed +/+ and −/− axenic amastigote cells from 48 hr culture were stained with DAPI and viewed under a fluorescent microscope. Right panel: pale blue (light gray) spots are kinetoplasts, larger dark blue (dark grey) regions are nuclei. Left panel: phase contrast image of the same field shown in the right panel (C) Transmission Electron Micrograph of *Leishmania* wild type (+/+) (1) and mutant (−/−) (2 and 3) axenic amastigotes after 48 hr in culture. Shown are one representative field for wild type (+/+) and two representative fields for centrin knockout mutants (−/−). K—kinetoplast, M—microtubules and N—Nucleus are indicated. All images original magnification: 400×. (D) Quantitative analysis of the number of DAPI stained kinetoplasts in the viable LdCEN$^{-/-}$ axenic amastigotes with increasing time in culture. Cells, with one, two or more than four kinetoplasts, were counted and individually plotted as percent of cells showing each number of kinetoplasts/cell. The results were obtained from at least 150 viable cells (cells not staining to tryphan blue) observed in each case. Data represent the mean±SD of three independent experiments.

FIG. 8 Percent of cells positive for the uptake of PI. FACS analysis of parasites of the +/+ (solid bars) and −/− (hatched bars) genotypes sampled over time after inoculation into axenic amastigote culture medium. Fluorescing cell populations were measured for PI at FL-3 channel. For each sample 10,000 fluorescent events were measured.

FIG. 9 (A) Percent of cells positive for PPL cleavage activity. FACS analysis of parasites analyzed in the above experiment (FIG. 6) were measured simultaneously for the PPL cleavage activity at FL-1 channel. (B) Percent of TUNEL positive +/+ and −/− axenic amastigotes at 0, 24 and 36 hr incubation periods. The culture at 0 hr time point indeed were the exponentially growing promastigote parasites used to initiate the axenic amastigote culture for the assay. At each time point at least 200 total cells were counted. Data represent the mean±SD of three independent experiments. *P<0.008 student's t-test. (C) TUNEL assay images of samples included in the cell counts in part E, observed under the fluorescence microscope. DAPI images false colored red (dark grey) show the staining of both the kinetoplasts and the nuclei (images 1 and 2). The TUNEL positive nuclei and kinetoplasts show green fluorescence (light grey) (images 3 and 4). DAPI and TUNEL images were merged and shown (images 5 and 6). All images original magnification: 1000×.

FIG. 10 (A) Percent infected macrophages (top panel), number of parasites per 100 total macrophages (middle panel) and number of parasites per infected macrophage (bottom panel) at various post-infection time points. Results from three independent experiments were averaged and plotted with error bars indicating the standard deviation. *P<0.005 and **P<0.0001 student's t-test. (B) Light microscopy of the human macrophages infected with the +/+ and −/− parasites incubated for 120 and 240 hr. Am—amastigotes; M—multinucleated parasites; P—phagolysosome in a macrophage. All images original magnification: 400×.

Figure 11B:
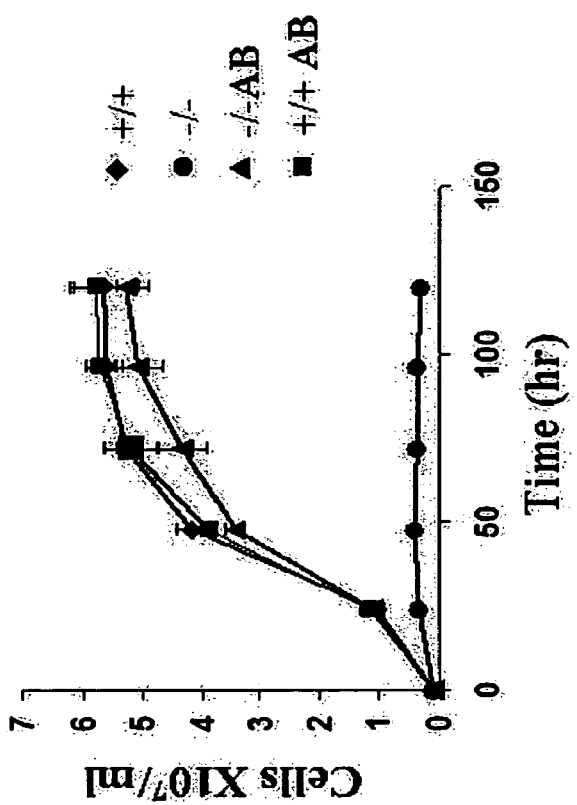

FIG. 11 (A) Western blot analysis on the cell lysate from axenic amastigotes of *Leishmania* wild type (+/+), LdCEN knockout (−/−), LdCEN knockout parasites with centrin added back by transfection of a centrin expression plasmid (pXG-PHLEO-LdCEN) (−/−AB) and wild type similarly over expressing centrin (+/+AB). Blots were developed using αLdCen Ab. (B) Growth analysis of the axenic amastigote parasites of the +/+, −/−, +/+AB and −/−AB. Data represent the mean±SD of three independent experiments.

FIG. 12 A, B Centrin sequence from different species of *Leishmania*. Nucleotide sequence for centrin isolated from *Leishmania donovani, Leishmania infantum, Leishmania amazonensis, Leishmania major, Leishmania mexicana*, and *Leishmania tropica*.

BRIEF DESCRIPTION OF THE SEQUENCES

| Sequence | SEQ ID NO. |
| --- | --- |
| *Leishmania donovani* centrin | SEQ ID NO: 1 |
| *Leishmania infantum* centrin | SEQ ID NO: 2 |
| *Leishmania amazonensis* centrin | SEQ ID NO: 3 |
| *Leishmania major* centrin | SEQ ID NO: 4 |
| *Leishmania mexicana* centrin | SEQ ID NO: 5 |
| *Leishmania tropica* centrin | SEQ ID NO: 6 |

DETAILED DESCRIPTION OF THE PREFERRED EMBODIMENT

Recently, we identified and cloned multiple centrin genes from *L. donovani*. Homologues of centrin have been shown to be involved in duplication and segregation of centrosomes in higher eukaryotes. Expression of *Leishmania* centrin correlates with the growth phase of the parasite. In order to understand the role of centrin in the parasite growth, we created *Leishmania* deficient in one of its centrin genes (LdCEN) by double homologous gene replacement. We found that centrin null mutants (LdCEN$^{-/-}$) had a selective growth arrest as axenic amastigotes and not as promastigotes. The axenic amastigotes showed failure of basal body duplication and failure of cytokinesis resulting in multinucleated 'large' cells. Flowcytometry analysis confirmed that the mutant parasites have a cell cycle arrest at the G2/M stage. Increased caspase like activity and concomitant TUNEL positivity was observed in centrin mutant amastigotes compared to wild type cells indicating the activation of programmed cell death pathway, which subsequently could result in loss of viable cells. When LdCEN$^{-/-}$ promastigotes were used to infect macrophage cells in culture, growth of the intracellular amastigotes was inhibited and large multinucleated parasite cells similar to those observed in vitro resulted. Upon re-expression of recombinant centrin in LdCEN$^{-/-}$ parasites, growth was restored in the mutant parasites similar to wild type parasites. These results demonstrate the direct involvement of centrin expression in *Leishmania* growth. Further, this is the first report where targeted disruption of a gene involved in cytokinesis leads to stage specific attenuation in a parasite. *Leishmania* centrin null mutants with a growth defect in axenic amastigotes are envisioned as being useful as an attenuated parasite vaccine against leishmaniasis.

Further Description Section I

The present invention is directed towards the provision of attenuated strains of *Leishmania*. The attenuated strains are useful for the preparation of immunogenic preparations including vaccines against disease caused by infection by a virulent *Leishmania* strain and as tools for the generation of immunological and diagnostic reagents.

In accordance with one aspect of the present invention, there is provided an attenuated strain of *Leishmania* wherein at least one gene of the strain contributing to virulence thereof and expressed in both the promastigote and amastigote stages of the life cycle of the strain has been functionally disabled by, for example, a deletion of at least a portion of the gene or by mutagenesis.

In another aspect of the invention, there is provided an attenuated strain of *Leishmania* wherein both wild-type copies of a gene of the strain contributing to virulence thereof have been functionally disabled. The gene contributing to the virulence of the strain in this aspect of the invention may be one expressed in both the promastigote and amastigote stages of the life cycle of the strain.

The gene may contribute to the ability of the strain to infect or survive within macrophages and, in a particular embodiment, may encode *Leishmania* centrin. The attenuated *Leishmania* strain may be selected from the group consisting of *Leishmania donovani, Leishmania infantum, Leishmania chagasi, Leishmania major, Leishmania tropica, Leishmania aethiopica, Leishmania braziliensis, Leishmania mexicana*, and *Leishmania amazonensis*.

The six species of *Leishmania* recognized to cause disease in humans (Table 1) are very similar morphologically but produce strikingly different pathological responses. The only feature common to all is the chronicity of disease manifestations. The infection may be predominantly visceral, as in visceral leishmaniasis or Indian kala-azar, or restricted to the skin, as with the chronic ulcer of Oriental sore, or spreading to the mucous membranes to produce the disfiguring South American espundia (Handman, E. et al. 2001 *Clinical Microbiology Review* 14:229-243.)

TABLE 1

Leishmania species pathogenic for humans, their vectors, host range and disease manifestations

| Species | Host range | Main vector | Disease manifestations |
|---|---|---|---|
| L. donovani (India and Africa) and related L. infantum (Mediterranean region, the Middle East, and Asia) and L. chagasi (South America) | Dogs, savannah rodents, humans | P. argentipes, L. longipalpis | Visceral leishmaniasis (kala azar), post-kala-azar dermal leishmaniasis (PKDL) |
| L. major | Desert and savannah rodents; Rhombomys, Psammomys, Arvicanthis | P. papatasi | Cutaneous leishmaniasis (rural, wet Oriental sore) |
| L. tropica | Humans | P. sergenti | Cutaneous leishmaniasis (urban, dry Oriental sore), visceral leishmaniasis |
| L. aethiopica | Rock hyrax | P. longipes | Cutaneous leishmaniasis, diffuse cutaneous leishmaniasis |
| L. braziliensis complex | Sloth, dog | L. umbratilis and many others | Cutaneous leishmaniasis, mucocutaneous leishmaniasis |
| L. mexicana complex, e.g., L. mexicana amazonensis | Forest rodents | L. flaviscutellata, L. olmeca | Cutaneous leishmaniasis, diffuse cutaneous leishmaniasis |

The sequence of *Leishmania donovani* centrin (centrin that has been deleted in *L. donovani*) is provided in GenBank accession number AF406767 and FIG. 12.

The sequences of centrins identical to *L. donivani* centrin found in other species are: *Leishmania infantum* centrin, *Leishmania amazonensis* centrin, *Leishmania major* centrin, *Leishmania mexicana* centrin, and *Leishmania tropica* centrin, all provided in FIG. 12.

In a further aspect, the present invention provides an immunogenic composition comprising the attenuated strains as provided herein. The immunogenic composition may be formulated as a vaccine for in vivo administration to a host, such as a primate including humans, to confer protection against disease caused by a virulent strain of *Leishmania*, including *Leishmania donovani, Leishmania infantum, Leishmania chagasi, Leishmania major, Leishmania tropica, Leishmania aethiopica, Leishmania braziliensis, Leishmania mexicana,* and *Leishmania amazonensis*.

In an additional aspect, the invention provides a method of generating an immune response in a host, such as a primate including humans, comprising administering thereto an immunoeffective amount of the immunogenic composition, as provided herein. In a particular aspect, the immunogenic composition may be formulated as a vaccine for in vivo administration to the host to confer protection against disease caused by a virulent strain of *Leishmania*, including *Leishmania donovani, Leishmania infantum, Leishmania chagasi, Leishmania major, Leishmania tropica, Leishmania aethiopica, Leishmania braziliensis, Leishmania mexicana,* and *Leishmania amazonensis*.

In yet an additional aspect, there is provided a method for producing a vaccine for protection against a disease caused by infection by a virulent strain of *Leishmania*, including *Leishmania donovani, Leishmania infantum, Leishmania chagasi, Leishmania major, Leishmania tropica, Leishmania aethiopica, Leishmania braziliensis, Leishmania mexicana,* and *Leishmania amazonensis*, and comprising administering the immunogenic composition as provided herein to a test host to determine an amount and frequency of administration thereof to confer protection against disease caused by infection by the *Leishmania* parasite and formulating the immunogenic composition in a form suitable for administration to a treated host, including humans, in accordance with said determined amount and frequency of administration.

In a further aspect of the invention, there is provided a method of forming an attenuated strain of *Leishmania* that comprises identifying a gene of a *Leishmania* strain contributing to the virulence thereof and expressed in both the promastigote and amastigote stages of the life cycle of the strain, and functionally disabling the gene.

These virulence genes may be functionally disabled by, for example, deletion or mutation, including insertional mutagenesis and, furthermore, the wild-type *Leishmania* gene may be replaced by the functionally disabled gene. The virulence genes may be functionally disabled by, for example, replacing the gene by a selectable antibiotic resistance gene by homologous recombination following transformation of the *Leishmania* organism with a fragment of DNA containing the antibiotic resistance gene flanked by 5'- and 3'-non-coding DNA sequences.

This method can be used to generate the attenuated variants of *Leishmania* and the residual pathogenicity of the attenuated variants can be assessed in mice and hamsters. Deletion of the genes that are selectively expressed results in an attenuated strain that cannot survive in humans but generates a protective immune response. Attenuated strains of *Leishmania* as provided herein would be useful as live vaccines against the diseases caused by *Leishmania*.

Advantages of the present invention include the provision of safe and attenuated strains of *Leishmania* for the preparation of immunogenic compositions including vaccines and for the generation of immunological and diagnostic reagents.

Further Description Section II

It is among the objects of the present invention to provide an improved *Leishmania* vaccine. More particularly it is a preferred object of the present invention to provide a live attenuated *Leishmania* vaccine.

In one aspect the present invention provides the use of a mutant *Leishmania* in the preparation of a vaccine, wherein the mutant *Leishmania* comprises a defective centrin gene, such that the mutant *Leishmania* is substantially incapable of expressing a functionally active form of centrin protein encoded by said gene A further aspect of the invention relates to the vaccine itself.

While the present description refers mainly to the use of promastigotes in the preparation of a vaccine, it is to be understood that pure amastigotes or amastigotes in mammalian cells may be used as alternatives.

The mutant *Leishmania* may be selected from all species of *Leishmania* including *Leishmania donovani, Leishmania infantum, Leishmania chagasi, Leishmania major, Leishmania tropica, Leishmania aethiopica, Leishmania braziliensis, Leishmania mexicana*, and *Leishmania amazonensis*.

A "defective centrin gene" is one that is substantially incapable of encoding for a native centrin protein or a functional equivalent thereof. Thus, a "defective centrin gene" means that the centrin gene has been modified by a deletion, insertion, substitution (or other change in the DNA sequence such as rearrangement) such that the centrin gene is generally incapable of expressing a functionally competent centrin protein from said gene. It will be appreciated that modification may also extend to the regulatory regions of the gene, providing that the result is that a functionally competent centrin protein encoded by the particular gene is not expressed.

The "defective centrin gene" may however be capable of expressing a defective centrin protein that is functionally inactive. Such a defective centrin protein may however be antigenic or immunogenic, such that a host may elicit an immune response to the defective centrin protein.

If the mutant is for example a *Leishmania donovani* mutant then said centrin gene is a single copy gene encoding said centrin protein.

The present inventors have now also identified or may identify the corresponding centrin gene in *Leishmania donovani, Leishmania infantum, Leishmania chagasi, Leishmania major, Leishmania tropica, Leishmania aethiopica, Leishmania braziliensis, Leishmania mexicana*, and *Leishmania amazonensis*, such that *Leishmania donovani, Leishmania infantum, Leishmania chagasi, Leishmania major, Leishmania tropica, Leishmania aethiopica, Leishmania braziliensis, Leishmania mexicana*, and *Leishmania amazonensis* centrin mutants may also be produced as described herein and used in the preparation of a vaccine.

Thus, in a further aspect the present invention provides a vaccine formulation comprising a mutant *Leishmania donovani, Leishmania infantum, Leishmania chagasi, Leishmania major, Leishmania tropica, Leishmania aethiopica, Leishmania braziliensis, Leishmania mexicana*, or *Leishmania amazonensis* wherein a centrin gene has been made defective as described herein.

Centrin genes of the present invention that are subsequently incapable of expressing a functionally competent centrin protein may be rendered dysfunctional by any one or more ways for example:

(i) A deletion of the entire centrin protein coding region of the centrin gene from a wild type *Leishmania* genome. The deletion should be such so as not to substantially affect the expression of other gene products from the *Leishmania* parasite genome.

(ii) A deletion of a portion of the centrin protein coding region from a wild type *Leishmania* genome. A "portion of the centrin protein coding region" means a polynucleotide fragment that by its deletion from the centrin protein coding region is sufficient to render any centrin protein or fragment or fragments thereof encoded and/or expressible thereby, substantially incapable of a physiological activity attributable to that of a functional centrin protein produced by a wild type parasite. The deleted portion of the centrin gene may be composed of a deletion of a small number of nucleotides, for example, 1, 2 or more nucleotides. Such deletions within the centrin gene can be achieved using recombinant DNA technology. Thus, the translational open reading frame (ORF) for a centrin gene can be altered resulting in the production of a protein that lacks the physiological functionality or functional competence of a centrin protein derived from wild type *Leishmania*. The skilled addressee will also appreciate that such deletions in the translational ORF of the centrin gene may also give rise to a dysfunctional gene that is substantially incapable of coding for a functionally competent centrin protein, truncated centrin protein or polypeptide fragment thereof. Such proteins/polypeptides, if produced, generally lack the functional competence typical of the full length centrin protein.

(iii) The deletion of the or a portion of the centrin gene as described in (i) or (ii) above will leave a "gap" in the centrin gene. A suitable polynucleotide such as a gene or gene fragment thereof may be inserted into the "gap". Gene insertions can include genes that express polypeptides capable of augmenting an immune response, such as mammalian cytokines, for example, γ interferon or other genes such as marker genes. Suitable marker genes may include but are not restricted to genes encoding enzymes, for example thymidine kinase, or genes encoding antibiotic resistance to such as, puromycin, tunicamycin, hygromycin, neomycin, phleomycin, nourseothricin and the like. Generally these genes, if any, may be employed in a centrin gene deletion. Mutants of the invention should be such so as not to cause substantial deleterious or long lasting side-effects to a recipient animal.

It is typical to utilize a system that generates drug resistance marker-exploiting mutants. Such a system may involve sequential rounds of targeted gene disruption using positive or negative selection. In the generation of centrin protein double allele null mutants, typically, each of said two single copy centrin genes will be targeted for disruption independently and subsequently multiple mutants will be generated. The hygromycin (hyg) gene may be used as a positive selectable marker for the antibiotic hygromycin. The viral HSV thymidine kinase gene (tk) may be used as a negative selectable marker in conjunction with the drug ganciclovir (Lebowitz, J. H. 1994 *Methods Cell Biol.* 45:65-78).

For example, wild type *Leishmania* may be transfected with a construct containing both the hyg and tk genes arranged in tandem in order to delete one allele of a centrin gene. Selection with hygromycin will allow transformants to be selected in which the particular centrin gene has been deleted as, for example, described previously (Mottram et al. 1996 *PNAS USA.* 93:6008-13) A second round of transfection would then be performed with a "null targeting fragment" containing centrin gene flanking DNA that will delete the hyg/tk DNA that has been integrated into the centrin locus. Cells in which the tk gene remains may then be killed by the ganciclovir drug, whereas mutants in which the centrin gene and the drug markers have been deleted will grow. In this manner one allele of the centrin gene will have been deleted and no exogenous DNA will remain in the centrin locus. The procedure will then be repeated for the second centrin allele as *Leishmania* is diploid, to produce a centrin gene null mutant. The entire procedure may then be repeated if necessary in order to produce a viable centrin gene double null mutant.

In a preferment there is provided a *Leishmania* centrin gene double null mutant comprising deletions in said centrin regions within the *Leishmania* genome. The deletion should be such that coding sequences for other gene products of the *Leishmania*, upstream and/or downstream from the centrin domains, are not substantially affected. That is to say that other gene products ordinarily having an immunogenic function and that are expressed in Leishmania substantially retain their immunogenic function.

The deletion generally has to be made in said centrin genes in positions such that any mutant Leishmania within a host cell retains a sufficient function to elicit an immune response in a host animal, such as a dog or human. If the prophylactic and/or therapeutic effect of an appropriate Leishmania mutant of the present invention is to be augmented, an appropriate adjuvant, such as a cytokine, for example, γ interferon (γ-IFN) can also be employed as a component of a vaccine or pharmaceutical composition of the invention.

Optionally, such centrin gene null Leishmania mutants may be further modified to express a dysfunctional form of a centrin protein, such as the centrin protein that is not expressed by the mutant. Thus, the mutant may express a centrin protein that is functionally inactive, but that is antigenic or immunogenic. For example, to produce an inactive centrin protein the active site can be changed by site-directed mutagenesis. This mutation should result in the production of full length centrin protein that is functionally inactive. The gene encoding the inactive centrin protein can then be re-introduced into a centrin gene null mutant by homologous recombination using unique sequence that flank the centrin gene.

In a further embodiment of the invention there is provided a host cell comprising a centrin gene null Leishmania mutant of the present invention. The host cell may for example be a macrophage or similar cell type known to those skilled in art.

Centrin gene null Leishmania mutants of the present invention may be applied directly to the cells of an animal in vivo, or by in vitro infection of cells taken from the said animal, which cells are then introduced back into the animal. Leishmania centrin gene null mutants may be delivered to various tissues of the animal body including muscle, skin or blood cells thereof. The Leishmania centrin gene null mutant may be injected into for example, muscle or skin using a suitable syringe.

Centrin gene null Leishmania mutants for injection may be prepared in unit dosage form in ampoules, or in multidose containers. The parasites may be present in such forms as suspensions, solutions, or emulsions in oily or preferably aqueous vehicles. For any parenteral use, particularly if the formulation is to be administered intravenously, the total concentration of solutes should be controlled to make the preparation isotonic, hypotonic, or weakly hypertonic. Non-ionic materials, such as sugars, are preferred. Any of these forms may further comprise suitable formulatory agents, such as starch or sugar, glycerol or saline. The compositions per unit dosage, whether liquid or solid, may contain from 0.1% to 99% of parasite material.

In a further embodiment of the invention there is provided a vaccine against Leishmania comprising a centrin gene-deficient Leishmania mutant. The vaccine of the invention may optionally include a further compound having an immunogenic function such as a cytokine, for example, γ interferon.

In a preferred presentation, the vaccine can also comprise an adjuvant. Adjuvants in general comprise substances that boost the immune response of the host in a non-specific manner. A number of different adjuvants are known in the art. Examples of adjuvants may include Freund's Complete adjuvant, Freund's Incomplete adjuvant, liposomes, and niosomes as described in WO 90/11092, mineral and non-mineral oil-based water-in-oil emulsion adjuvants, cytokines, short immunostimulatory polynucleotide sequences, for example, in plasmid DNA containing CpG dinucleotides such as those described by Sato, Y. et al. 1996 Science 273: 352-4.

In addition, the vaccine may compromise one or more, suitable surface-active compounds or emulsifiers, e.g. Span or Tween.

In a further aspect of the invention there is provided the use of a centrin gene-deficient Leishmania mutant as described herein for the manufacture of a vaccine for the prophylaxis and/or treatment of leishmaniasis. Most preferably, the use is in dogs or humans.

In a further aspect of the invention there is provided a method of treating animals that comprises administering thereto a vaccine composition comprising a centrin gene-deficient Leishmania mutant as described herein to animals in need thereof. Preferably, the animals are dogs or humans. Naturally, the vaccine formulation may be formulated for administration by oral dosage, by parental injection or otherwise.

The invention also provides a process for preparing a Leishmania vaccine, which process comprises admixing a centrin gene-deficient Leishmania mutant as herein described with a suitable carrier or adjuvant.

The mode of administration of the vaccine of the invention may be by any suitable route that delivers an immunoprotective amount of the parasite of the invention to the subject. However, the vaccine is preferably administered parenterally via the intramuscular or deep subcutaneous routes. Other modes of administration may also be employed, where desired, such as oral administration or via other parental routes, e.g., intradermally, intranasally, or intravenously.

Generally, the vaccine will usually be presented as a pharmaceutical formulation including a carrier or excipient, for example an injectable carrier such as saline or pyrogenic water. The formulation may be prepared by conventional means. It will be understood, however, that the specific dose level for any particular recipient animal will depend upon a variety of factors including age, general health, and sex; the time of administration; the route of administration; synergistic effects with any other drugs being administered; and the degree of protection being sought. Of course, the administration can be repeated at suitable intervals if necessary.

Targeted Disruption of the Centrin Gene Leads to Amastigote Stage Specific Attenuation of Growth in *Leishmania donovani*

Generation of LdCEN Null *L. donovani* Promastigotes

Homologous recombination was utilized to delete (knock-out) LdCEN in the diploid organism *L. donovani*. To delete both alleles of the centrin gene we used two recombinant DNA fragments with two different antibiotic resistant genes as markers: hyg gene that confers resistance to hygromycin B and neo gene that confers resistance to G418 (FIG. 1). The marker genes were flanked at the 5' and 3' ends with the 5' and 3'UTRs of centrin gene respectively for the homologous recombination. Construction of the targeting fragments is described in the legend to FIG. 1. Disruption of the two alleles was carried out step by step, by first using the hyg construct and then using the neo construct to obtain a double knockout. The clones obtained after each transfection were screened for the deletion of centrin by both PCR analysis using primers specific to centrin, hyg and neo genes and by Southern blot analysis using labeled gene specific probes for centrin, hyg and neo (FIG. 2A). FIG. 2B, lane 9 shows complete loss of the coding region of the LdCEN in double knockout mutants. Loss of centrin expression in the parasite was also confirmed by Northern blot analysis using LdCEN gene as probe and by Western blot analysis using anti-LdCen antibody. The centrin disrupted parasite (LdCEN$^{-/-}$) neither expresses the mRNA for centrin nor centrin protein (FIG. 2C, lane 3). LdCEN–/– promastigotes were then propagated and used for further characterization.

LdCEN$^{-/-}$ Parasite does not Grow as an Axenic Amastigote

Our earlier studies had shown that transfected *L. donovani* expressing N-terminal deleted centrin grew slower compared to wild type cells in vitro (Selvapandiyan, A. et al. 2001 *J Biol Chem.* 276:43253-43261). In the present disclosure deletion of both the alleles of centrin did not affect the growth of null mutant promastigotes (FIG. 3A). However, differences in growth were seen between wild type and centrin null mutant axenic amastigotes (FIG. 3B). The parasites were grown both as promastigotes and axenic amastigotes in the absence of antibiotics except the single knockout (+/−) that was grown in the presence of hygromycin B in order to avoid hyg gene's elimination by the duplication of the single centrin allele. The promastigote as well as axenic amastigote form of the parasite with a single centrin allele knockout (+/−) showed a growth pattern similar to that of the wild type control (+/+) (FIGS. 3A and B). When the actively growing centrin null mutant promastigotes (−/−) were transferred to the axenic amastigote medium, the culture showed a slight increase in cell number only in the first 24 hours, a period required for the promastigotes to differentiate into axenic amastigotes. There after there was no growth in the culture and after 96 hr incubation, a gradual decrease in cell number occurred (FIG. 3B). It is interesting to note when a day 2 axenic amastigote culture of LdCEN$^{-/-}$ was switched to promastigote medium (with 100 fold dilution), the parasites could differentiate into promastigotes, albeit after a long lag period of 8 days. However, if axenic amastigotes of LdCEN$^{-/-}$ after 7 days in culture were shifted to promastigote medium, it was not possible to restore the growth.

LdCEN$^{-/-}$ Axenic Amastigote Cells Fail to Duplicate Their Basal Bodies

Figure 4:
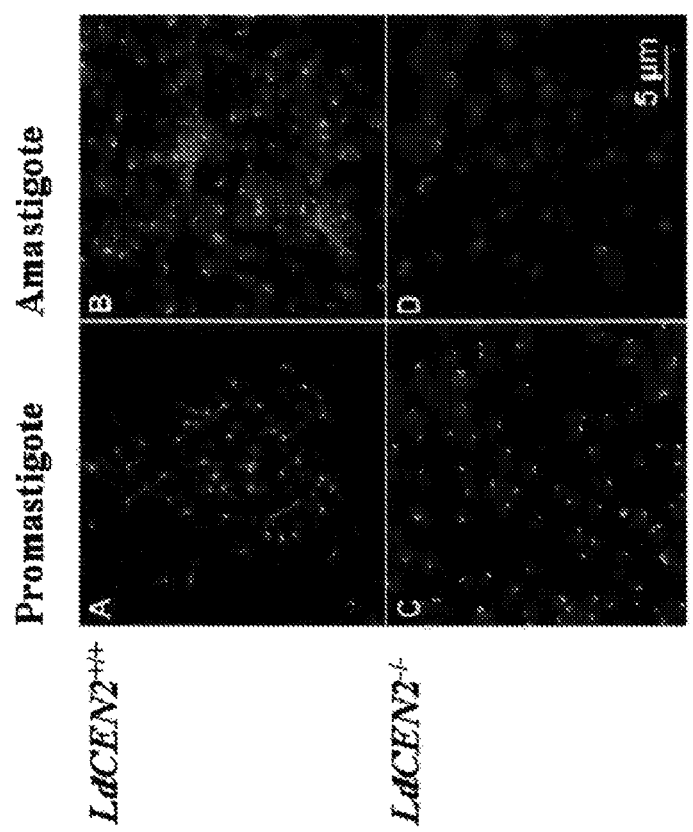
Figure 5:
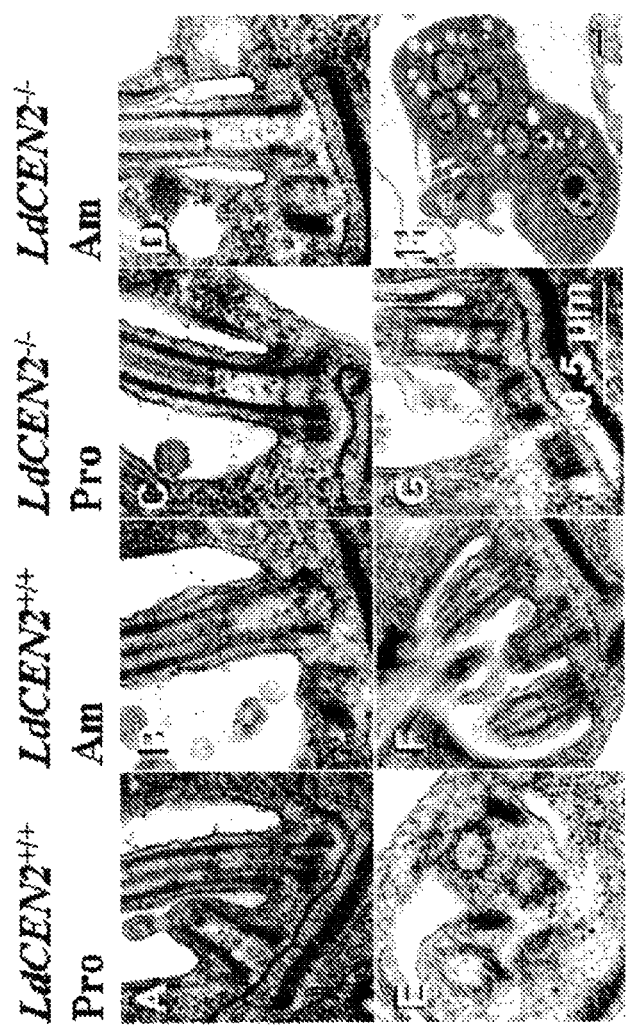

Indirect immunofluorescence localization of centrin using a pan-centrin monoclonal antibody (20H5) in both wild type and LdCEN deficient promastigote and axenic amastigote cells is illustrated in FIG. 4. Both wild type and LdCEN deficient promastigote cells showed conspicuous localization of centrin at the base of emergent flagella as one or two bright spots, in addition to diffuse staining along the flagellar axoneme (FIG. 4A-B). In axenic amastigote cells, however, consistent localization of centrin at the flagellar base was seen only in wild type cells (FIG. 4C). Discrete centrin localization was largely absent in axenic amastigote cells deficient for LdCEN (FIG. 4D).

High-resolution electron microscopy of the flagellar apparatus was conducted in order to determine if specific alterations in basal bodies or associated structures could be distinguished in LdCEN deficient promastigote or axenic amastigote cells (FIG. 5A-D). Thin sections through the flagellar pocket revealed one or two basal bodies in promastigote and axenic amastigote cells that were essentially indistinguishable between the wild type and LdCEN$^{-/-}$ cells. Further analysis demonstrated that multiple basal bodies (three or four) could be found in individual wild type promastigote and amastigote cells and in LdCEN deficient promastigote cells (FIG. 5E-G). However, despite extensive analysis of sampled material, in no instance were more than two basal bodies found in LdCEN$^{-/-}$ deficient amastigote cells (FIG. 5H). Together with the immunofluorescence analysis these observations indicate that expression of LdCen-p is required for basal body duplication in axenic amastigote cells, while basal body duplication in promastigote cells can proceed in the absence of LdCen-p, presumably through the action or compensation by other *Leishmania* centrins.

Figure 6:
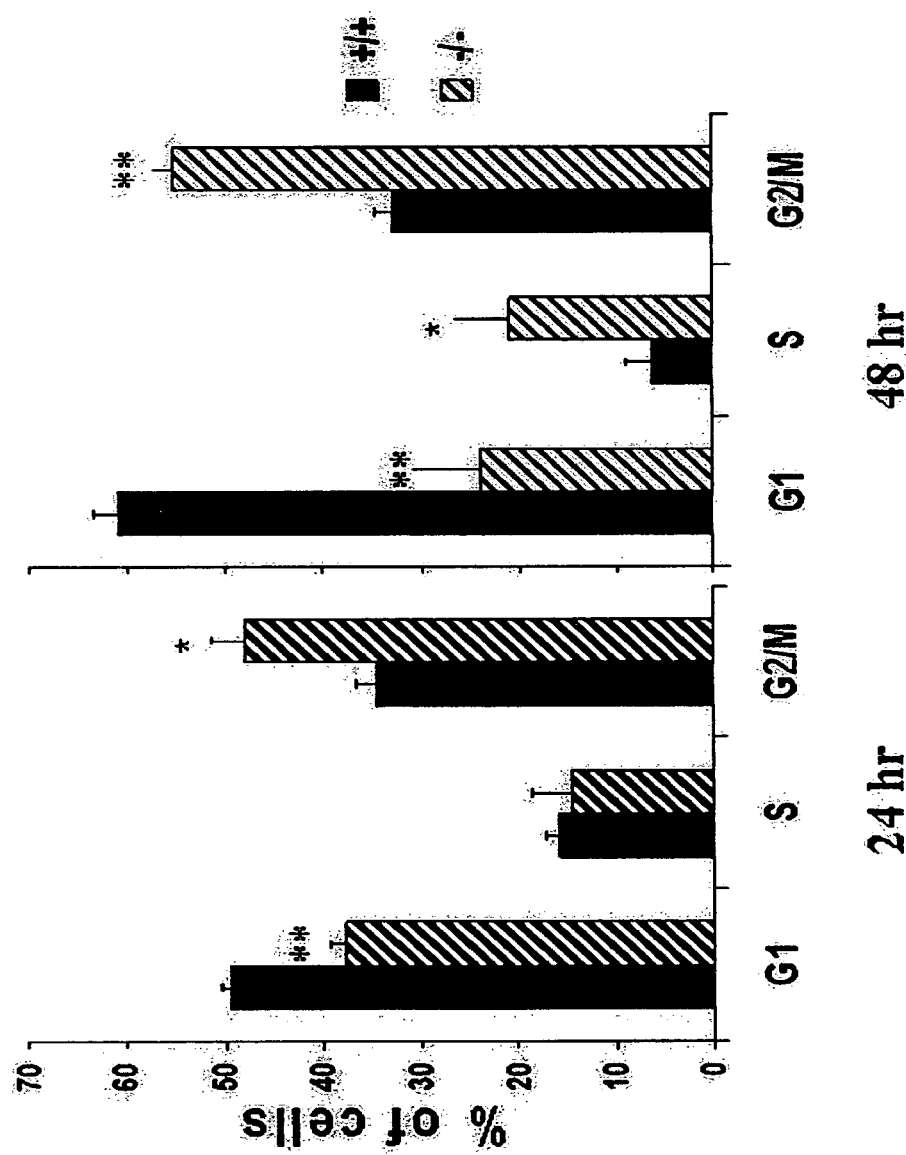

LdCEN$^{-/-}$ Axenic Amastigote Cells Accumulate at the G2/M Stage of the Cell Cycle To analyze the cause of the arrest of the growth of the axenic amastigote cells of LdCEN$^{-/-}$, the axenic amastigote cultures at 24 hr and 48 hr time points were subjected to cell cycle analysis using flowcytometry. At 24 hr culture, there were significantly less LdCEN$^{-/-}$ axenic amastigotes in the G1 phase and significantly more in the G2/M phase compared to wild type axenic amastigotes (FIG. 6). This difference became increasingly significant in cells after 48 hrs of culture. Further, we also observed more LdCEN$^{-/-}$ cells in S phase.

Figures 7C, 7D:
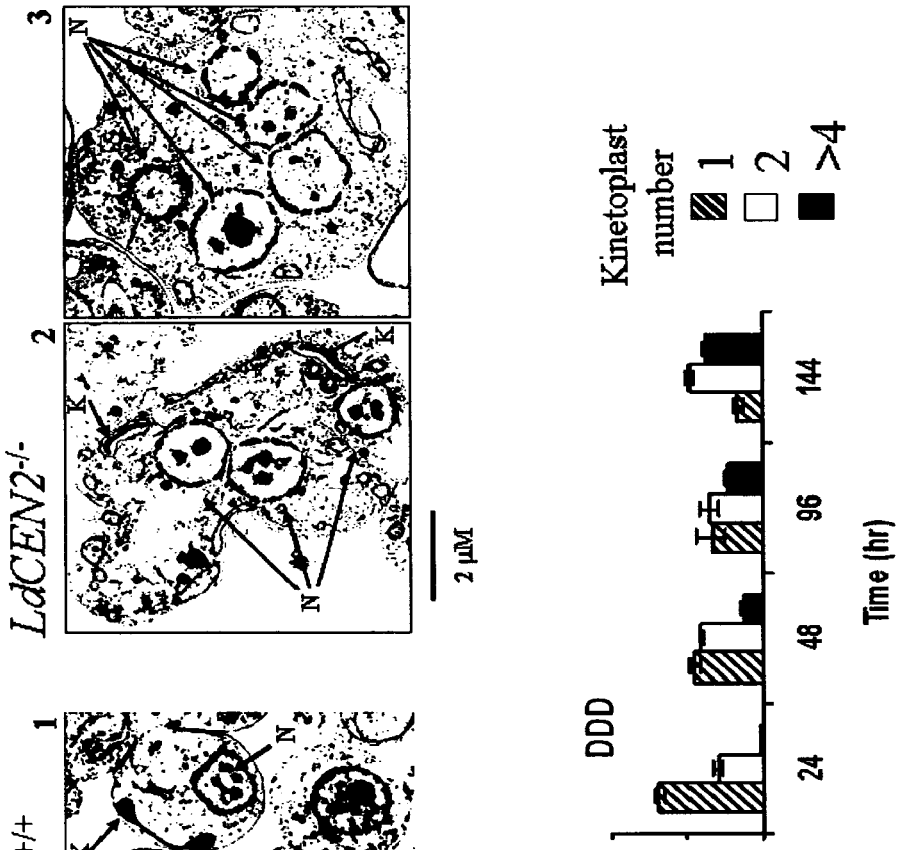

A characteristic feature of *L. donovani* axenic amastigotes in culture is that the cells form huge cell aggregates (FIG. 7A). Under the light microscope, LdCEN$^{-/-}$ axenic amastigotes on day 2 showed fewer cells with much smaller cell aggregates compared to the wild type axenic amastigotes (FIG. 7A). Many cells in this culture were larger in size. In order to look at the nuclei of these cells, 2 days old cultures were dispersed to individual cells, stained with DAPI and observed under the fluorescence microscope. All wild-type axenic amastigotes cells showed a single nucleus with one kinetoplast (FIG. 7B upper panel). However, the LdCEN deficient axenic amastigotes showed cells with multiple nuclei (FIG. 7B lower panel). A large proportion of cells showed two nuclei and two kinetoplasts per cell. These cells were indeed at least twice the size of the uninucleated cells. There were also cells with 4 nuclei and 4 kinetoplasts and displaying much larger cell size (FIG. 7B). To obtain a more detailed picture of the nuclei and their relationship to the plasma membrane in these multinucleated cells, LdCEN$^{-/-}$ axenic amastigotes were subject to electron microscopic analysis (FIG. 7C). The large cells were multinucleated with more than one kinetoplasts. These cells were highly amoebiotic in shape as opposed to the wild type control cells that are spherical (FIG. 7C; 2 and 3). Few of the multinucleated cells, probably the older ones, displayed condensed nuclei, a feature of cells undergoing apoptosis.

In order to quantitate the multinuclear status of the LdCEN$^{-/-}$ axenic amastigotes, we counted cells stained with DAPI in the fluorescent microscope. As DAPI stained the kinetoplasts brighter than the nuclei, the number of kinetoplasts per cell was counted with increasing time of culture of the LdCEN$^{-/-}$ axenic amastigote cells. The analysis showed a progressive increase of multi-kinetoplast cells with time in axenic amastigote culture for the centrin knockout parasites (FIG. 7D). There was a gradual decrease in the number of cells having a single kinetoplast (FIG. 7D).

Figure 8:
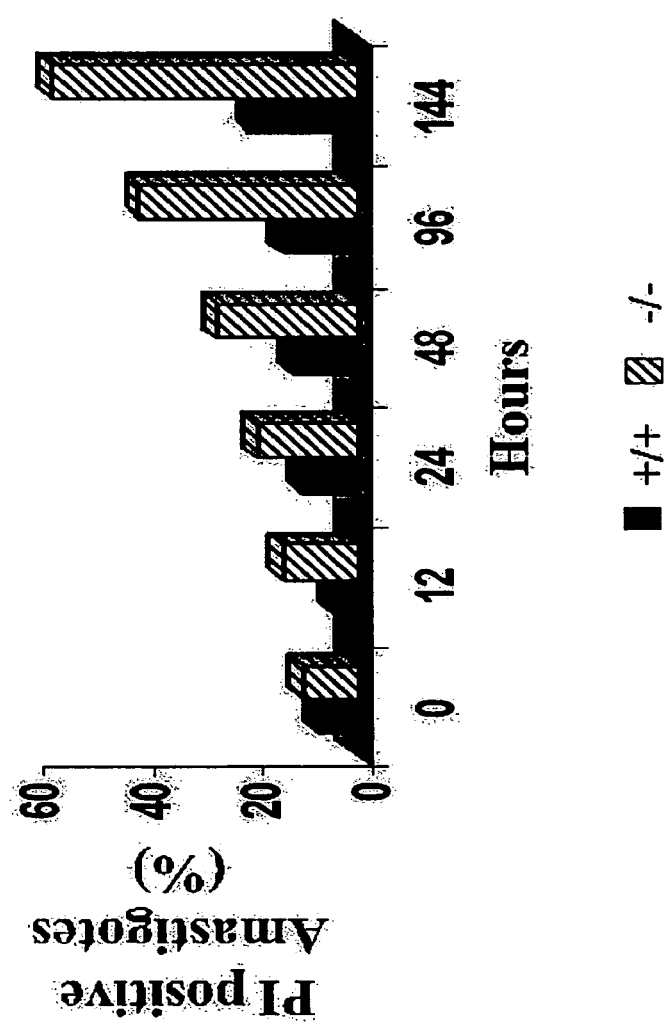

While counting the kinetoplasts, simultaneously we observed that there was also an increase in the number of cells without kinetoplasts in the culture over time. An increased uptake of tryphan blue staining was observed in cells, which did not possess either kinetoplasts or nuclei. Considering such cells as dead cells, they were scored separately by propidium iodide (PI) staining and analyzing using FACS. It is known that PI is taken up by only those cells whose plasma membrane integrity is compromised (Lee, N. et al. 2002 *Cell Death Differ* 9:53-64). Results showed that there was a progressive increase in the number of dead cells in LdCEN$^{-/-}$ axenic amastigote culture over time (FIG. 8). The centrin deficient parasites showed 3 fold more PI positive cells than the wild type control parasites after 144 hr culture as axenic amastigotes (FIG. 8).

LdCEN$^{-/-}$ Axenic Amastigote Cells Initiate Programmed Cell Death After the Growth Arrest Since there was no increase in the number of LdCEN$^{-/-}$ axenic amastigotes in culture with time and cells were becoming PI positive, we wanted to determine the type of death pathway the multinucleated axenic amastigotes undergo. The axenic amastigotes of LdCEN$^{-/-}$ or wild type cells were analyzed for caspase-like activity, which has been indicated as a marker for the apoptotic death pathway in *L. donovani* (Arnoult, D. et al. 2002 *Cell Death Differ* 9:65-81; Lee, N. et al. 2002 *Cell Death Differ* 9:53-64). The percentage of cells showing caspase like activity was measured by FACS analysis using fluorescent caspase substrate PhiPhiLux (PPL). The results showed that there were more PPL positive cells in the LdCEN$^{-/-}$ parasites in the first two days in culture than in the wild type control (FIG. 9A). The level of PPL cleavage activity gradually decreased after 48 hr of incubation. Whereas, in control, the increase in the level of PPL cleavage activity was observed only when the cells reached the stationary phase of growth in culture, as was previously observed by investigators (Lee, N. et al. 2002 *Cell Death Differ* 9:53-64). As further evidence of programmed cell death in the centrin disrupted cells, TUNEL assay was carried out on the cells that were growing in culture for 24 and 36 hr to identify cells with the fragmented DNA characteristic of the nuclei of apoptotic cells (Lee, N. et al. 2002 *Cell Death Differ* 9:53-64). Few TUNEL positive cells were observed in the wild type cells (FIG. 9B). In contrast, in the LdCEN$^{-/-}$ axenic amastigotes a much greater percentage of cells showed TUNEL positivity (FIG. 9B). FIG. 9C (image 6) shows the fluorescent microscopic picture of LdCEN$^{-/-}$ axenic amastigote cells that are both TUNEL positive and DAPI positive. Thus the increase in PPL cleavage activity and the increase in the number of TUNEL positive cells indicated that the LdCEN$^{-/-}$ axenic amastigotes initiate programmed cell death after they become multinucleated and stop growing.

LdCEN$^{-/-}$ Parasites do not Survive in Macrophages

Figure 10A:
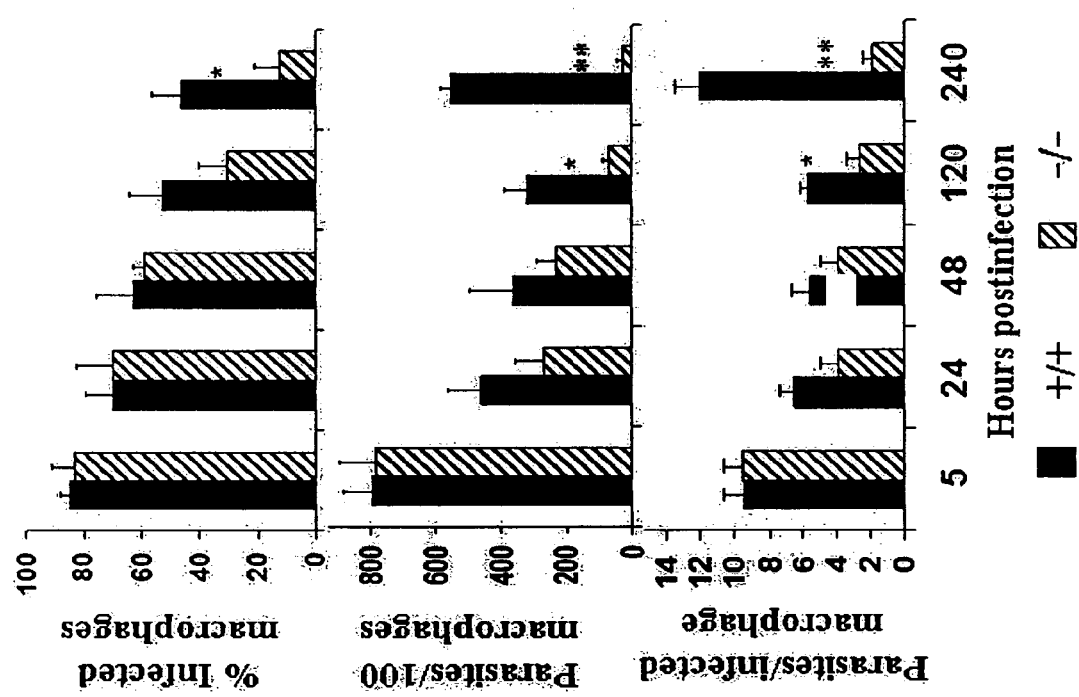
Figure 10B:
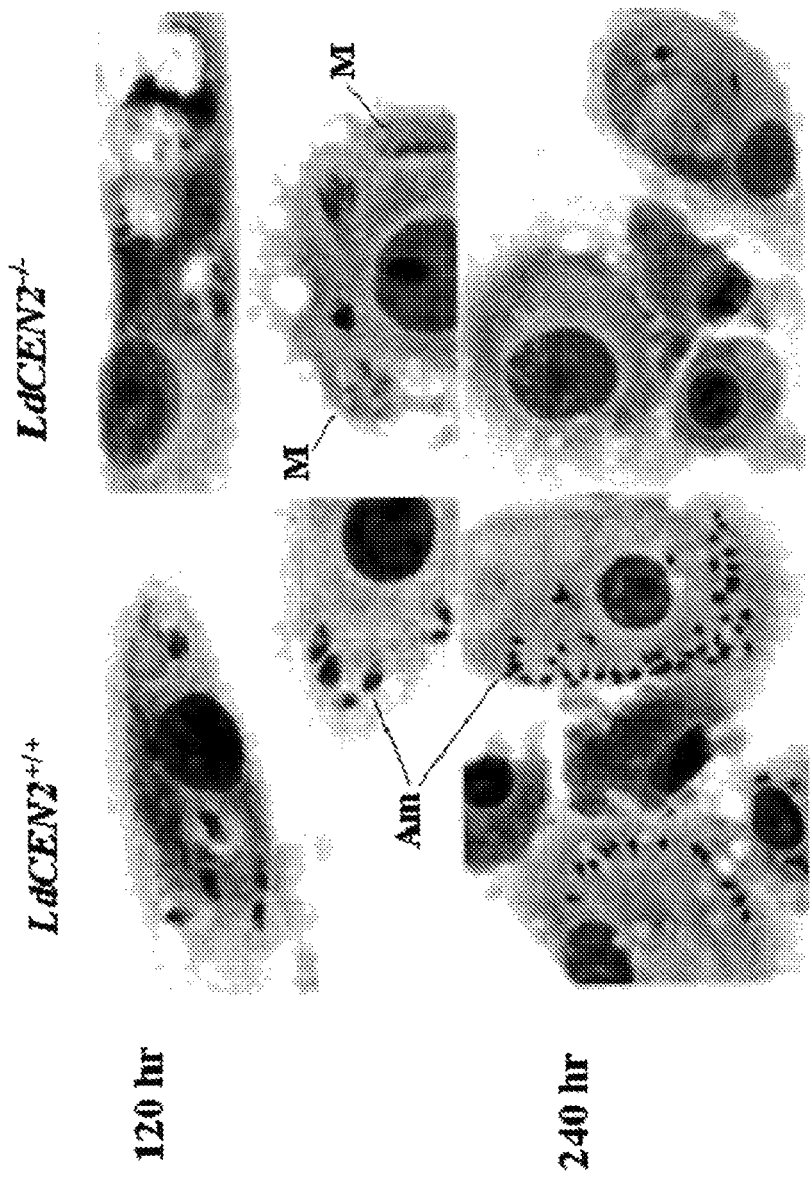

Since the centrin deficient *L. donovani* do not grow as an axenic amastigote in vitro, we examined their survivability in macrophages. To this end, human monocytes newly differentiated in vitro into macrophages by macrophage colony stimulating factor (M-CSF) were inoculated with stationary phase cultures of wild type and LdCEN$^{-/-}$ promastigotes (FIG. 10). Results at 5 hr post infection (p.i.) showed that the percent of macrophages that take up the parasites was similar (>80%) in macrophages inoculated with both types of parasites (FIG. 10A top panel). These macrophages were subsequently examined at 24, 48, 120 and 240 hr p.i. and the percent of infected macrophages was calculated. The percent of infected macrophages with LdCEN$^{-/-}$ parasite decreased to as low as 12% at 240 hr. Whereas, at the same time, 46% of the macrophages were infected with the control parasites (FIG. 10A, top panel). The macrophages, then, were scored for the parasite load (number of parasites per 100 macrophages). Significant difference was observed between the wild type control and the LdCEN$^{-/-}$ transfectants at 120 and 240 hrs p.i. (FIG. 10A, middle and lower panels). At the 240 hr time point, the total number of amastigotes per 100 macrophages was ~550 for the wild type transfectants and only ~26 for the macrophages transfected with the mutant parasite (FIG. 10A middle panel). The number of parasites per infected host cell at 240 hr p.i. was 12 for wild type parasite and 1.8 for the mutant parasites (FIG. 10A lower panel). After 312 hr p.i., no mutant parasite was seen in the macrophages. These results indicated that the centrin deficient parasites do not survive in the macrophages in vitro. Further, LdCEN$^{-/-}$ parasites that were taken up by macrophages developed into multinucleated large cells after 120 hr of culture (FIG. 10B). Wild type control cells did not become multinucleated in macrophages (FIG. 10B).

Figure 11A:
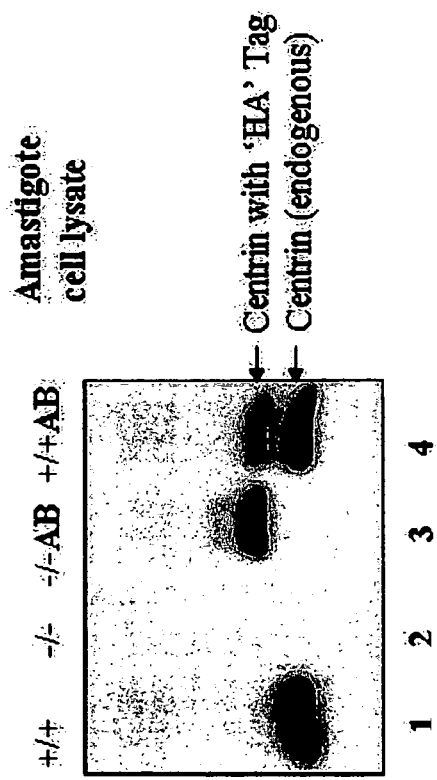

Reversal of Growth Inhibition by Centrin Expression in the LdCEN$^{-/-}$ Parasites To confirm that disruption of centrin gene expression was the specific cause of growth inhibition in LdCEN$^{-/-}$ axenic amastigotes, episomal expression of centrin in the knockout parasites was investigated. The recombinant plasmid (pXG-PHLEO-LdCEN) transfected axenic amastigotes that are adapted to grow in presence of Phleomycin (150 µg/ml) showed the expression of recombinant centrin protein (tagged with haemagglutinin tag) (FIG. 11A Lane 3). The rate of culture growth (FIG. 11B) and the morphology of the cell as seen under the microscope of the centrin re-expressing LdCEN$^{-/-}$ knockout axenic amastigotes were similar to the wild type cells. There were no multinucleated cells in such axenic amastigote culture. These studies demonstrated that re-expression of transfected centrin in LdCEN$^{-/-}$ parasites was able to reverse the growth defect seen in LdCEN$^{-/-}$ axenic amastigotes.

Discussion

The parasites of the order kinetoplastida, which infect humans, animals and plants, are considered to be one of the earliest eukaryotes. Conventional cellular organelles of these parasites can exhibit extreme features rarely seen in other organisms (Bastin, P. et al. 2000 *Microbes Infect* 2:1865-1874). The possible role of one such organelle, the basal body apparatus in the parasite life cycle is still obscure. We recently cloned and characterized a basal body protein 'centrin' in *L. donovani*, a causative agent of visceral leishmaniasis (Selvapandiyan, A. et al. 2001 *J Biol Chem.* 276:43253-43261). Centrin in *Leishmania* is a calcium binding protein implicated to be involved in growth/cell division of the parasite (Selvapandiyan, A. et al. 2001 *J Biol Chem.* 276:43253-43261) as has been indicated in higher eukaryotes (Pastrana-Rios, B. et al. 2002 *Biochemistry* 41:6911-6919; Salisbury, J. L. et al. 2002 *Curr Biol* 12:1287-1292; Wiech, H. et al. 1996 *J Biol Chem* 271:22453-22461). To define the decisive role of centrin in this parasite, we aimed at disrupting the centrin gene in *L. donovani*. Since *Leishmania* is diploid throughout in its life cycle, we adopted deletion of the centrin gene using two antibiotic resistant targeting genes. One potential problem for gene targeting for Trypanosomatid genes is, that, most of the proteins are encoded by arrays of multiple genes (Cruz, A. et al. 1991 *PNAS USA* 88:7170-7174). Since our earlier work had indicated that LdCEN is a single copy gene in the *Leishmania* genome (Selvapandiyan, A. et al. 2001 *J Biol Chem.* 276:43253-43261), we could disrupt the gene by the deletion of its alleles with hyg and neo constructs. The expression of centrin in *L. donovani* correlates with active growth of both promastigotes and axenic amastigotes in vitro (Selvapandiyan, A. et al. 2001 *J Biol Chem.* 276:43253-43261). Therefore we wanted to explore the effect of LdCEN deletion on the growth of the parasite. Parasites disrupted for a single LdCEN allele did not show any significant difference in their growth compared to control. The growth of the centrin double allele null mutant parasite, as promastigote was not affected in vitro. However, the growth of the axenic amastigote was significantly affected both in vitro as well as in the human macrophages. Upon re-expressing centrin in the mutant parasite through an episome, the growth inhibition in the axenic amastigote stage was abolished and the cells resumed normal growth. These experiments extend the importance of this gene for the growth of the parasite, mainly for the amastigote form.

Analysis by indirect immunofluorescence demonstrated centrin localization at the flagellar base in wild type and LdCEN$^{-/-}$ promastigote cells and in wild type amastigote cells. Axenic amastigote cells lacking the LdCEN gene and LdCen-p expression showed greatly reduced centrin fluorescence in most cells. Electron microscopy showed that flagellar apparatus and basal body structure was essentially indistinguishable between wild type and LdCEN$^{-/-}$ cells, albeit basal body duplication was evident only in promastigote and wild type axenic amastigote cells. These observations identify centrin in the normal duplication process of amastigote basal bodies and indicate that centrin function is either substituted or compensated for by other *Leishmania* centrins in the LdCEN$^{-/-}$ promastigote stage cells.

We further analyzed the cause of the growth defect through cell cycle analysis of the LdCEN$^{-/-}$ axenic amastigote. The flowcytometry analysis on LdCEN$^{-/-}$ axenic amastigote culture showed a significantly greater number of cells in the G2/M cell cycle stage. Both light and electron microscopy revealed that beyond 48 hr of incubation, many of these cells were large, without definite shape and with either two or more nuclei and with as many kinetoplasts. The multinucleated nature indicates the lack of cytokinesis in these cells. Gene silencing for HsCEN2 via RNAi in cultured HeLa cells results in failure of centriole duplication during the cell cycle and the cells give rise to multinucleate cells and finally die (Salisbury, J. L. et al. 2002 *Curr Biol.* 12: 1287-1292). A similar result also was noticed upon silencing the centrin gene by RNAi in *Chlamydomonas* (Koblenz, B. et al. 2003 *J Cell Sci* 116:2635-2646). The interference in the cytokinesis in centrin RNAi cells of *Chlamydomonas* was due to the presence of aberrant numbers of basal bodies that were separated from the spindle poles. Several mechanisms can explain failed cell division. Basal body/centriole duplication occurs once per cell division, and failed duplication or over production of these organelles would lead to aberrant cell division phases (Koblenz, B. et al. 2003 *J Cell Sci* 116:2635-2646; Salisbury, J. L. 2003 *Curr Biol* 13:R88-90; Salisbury, J. L. et al. 2002 *Curr Biol,* 12:1287-1292). These results demonstrate a requirement for centrin in the cytokinesis during mitosis and also shed some light on the differences in the molecular mechanism of cell division between the two stages of the parasite. The occurrence of a progressive increase in the number of multinucleated cells, closely followed by an increase in the number of dead cells indicates that the axenic amastigotes of the LdCEN$^{-/-}$ parasite die after going through a few rounds of nuclear divisions without cytokinesis. Basal bodies and centrioles share the same highly conserved ultrastructure of nine triplet microtubules forming a cylinder (Lechtreck, K. F. and Bornens, M. 2001 *Eur J Cell Biol* 80:631-641). The requirement of Human centrin 2 in centriole duplication, as well as a role in organizing spindle pole morphology and in the completion of cytokinesis was previously reported (Salisbury, J. L. et al. 2002 *Curr Biol.* 12:1287-1292). Similarly, by the present disclosure we observed the requirement of centrin for the completion of cytokinesis in *Leishmania*. The mechanism by which centrin involvement in the basal body duplication and in organizing other cytoskeletal morphology needs to be studied in this evolutionarily primitive organism (*L. donovani*), using centrin null mutant parasites.

Since we observed no growth in multinucleated LdCEN$^{-/-}$ axenic amastigotes and an increased number of cells permeable to PI, an indication of cell death in such cells, we analyzed the mode of cell death in such cells. Previously investigators have shown that cell growth arrest at saturation densities in culture leads to programmed cell death in *Leishmania* (Lee, N. et al. 2002 *Cell Death Differ* 9:53-64). In the present disclosure, we observed an increased PPL cleavage activity and TUNEL positivity in centrin deficient axenic amastigotes, which indicates that these cells are initiating the apoptotic pathway once cell division is disrupted.

The differential effect of centrin gene knockout in amastigotes is unique and surprising. We have evidence that LdCen-p is encoded by a single copy gene (Selvapandiyan, A. et al. 2001 *J Biol Chem.* 276:43253-43261). In addition, the level of expression of LdCen protein was similar in both promastigotes and axenic amastigotes (Selvapandiyan, A. et al. 2001 *J Biol Chem.* 276:43253-43261). However, we also had observed the existence of more than one centrin type in *L. donovani* (Selvapandiyan, A. et al. 2001 *J Biol Chem.* 276: 43253-43261). Recently, we observed additional centrin related genes in *Leishmania major* in the genome data bank. Therefore it is possible that different centrin genes, which may have a stage specific differential expression, could complement centrin function only for promastigotes in the LdCEN disrupted parasite. Alternatively the existence of amastigote specific growth regulating protein(s) that require interaction with centrin, could fail to function in the LdCEN$^{-/-}$ amastigotes. In our earlier report describing the dominant negative effect in the slow growing parasites expressing N-terminal deleted centrin, we had speculated about protein interaction involving *L. donovani* centrin and some yet unknown proteins (Selvapandiyan, A. et al. 2001 *J Biol Chem.* 276:43253-43261). In yeast, proteins KAR1 and CDC31 (yeast centrin) are required for the initial stages of spindle pole body duplication (Vallen, E. A. et al. 1994 *Genetics* 137:407-422). By immunofluorescence microscopy the interaction between these two proteins have been demonstrated in vivo (Biggins, S. and Rose, M. D. 1994 *J Cell Biol* 125:843-852). However, in contrast to the stage specific growth inhibition observed with the LdCEN$^{-/-}$ *Leishmania* (present disclosure), both promastigote and the amastigote stages were equally affected when N-terminal deleted centrin was expressed in the parasite (Selvapandiyan, A. et al. 2001 *J Biol Chem.* 276:43253-43261). Discovery of a novel centrin-binding partner, Sfi1p, lends new insight into the functional properties of centrin (Kilmartin, J. V. 2003 *J Cell Biol* 162: 1211-1221; Salisbury, J. L. 2004 *Curr Biol* 14:R27-29). Sfi1 protein binds multiple centrin molecules along a series of internal repeats, and the Sfi1p/centrin complex forms $Ca^{2+}$-sensitive contractile fibers that function to orient or position centrioles/basal bodies and to alter centrosome structure. Genetic analysis in yeast and *Chlamydomonas* and centrin ablation by siRNA or gene knockout clearly demonstrates that centriole/basal body duplication depends on proper Sfi1p/centrin function (see Salisbury, J. L. 2004 *Curr Biol* 14:R27-29, for review). Taken together these results predict a very complex mode of function and regulation of centrin in this evolutionarily primitive parasite, *Leishmania*. The present disclosure, however, demonstrates that LdCen protein is essential for the parasite to survive, especially for the amastigote stage.

Similar studies of gene knockouts for various enzyme cell surface and transporter proteins and the effect on virulence of the null mutant *Leishmania* parasites have been carried out by different laboratories. Examples are: dihydrofolate reductase-thymidylate synthase (Cruz, A. et al. 1991 *PNAS USA* 88:7170-7174; Titus, R. G. et al. 1995 *PNAS USA* 92:10267-10271), pteridine reductase 1 (Bello, A. R. et al. 1994 *PNAS USA* 91:11442-11446; Cunningham, M. L. et al. 2001 *Science* 292:285-287), lipophosphoglycan (Spath, G. F. et al. 2000 *PNAS USA* 97:9258-9263; Spath, G. F. et al. 2003 *PNAS USA* 100:9536-41) and leishmanolysin genes (Joshi, P. B. et al. 2002 *Mol Biochem Parasitol* 120:33-40) in *L. major*, and the glucose transporter gene family (Burchmore, R. J. et al. 2003 *PNAS USA* 100:3901-3906) in *L. mexicana* and ornithine decarboxylase (Jiang, Y. et al. 1999 *J Biol. Chem.* 274: 3781-3788), and spermidine synthase (Roberts, S. C. et al. 2001 *Mol Biochem Parasitol* 115:217-226) in *L. donovani*. In all the above studies, the gene knockout has affected equally both the promastigote and amastigote stages of the parasite. However, interestingly, in this disclosure we observed a differential effect that *L. donovani* centrin gene disruption affects selectively only the growth of the amastigote stage of the parasite both in vitro and inside the human macrophages. This is the first report that describes a gene knockout for a cytoskeletal structural protein in *Leishmania* and the importance of such a gene for the growth of the parasite. The practice of gene knockout realized for centrin in *L. donovani* can be applied readily for other *Leishmania* sp. that have a high degree of genome sequence conservation and cause similar visceral leishmaniasis, e.g., *L. infantum* and *L. chagasi*. In addition, inactivation of the centrin gene in the amastigote form of other related *Leishmania* species (*L. major, L. braziliensis*), which cause other forms of leishmaniasis, such as cutaneous and mucocutaneous diseases, is obvious as being utilized in the development of attenuated strains for these other species of *Leishmania*. Such attenuated strains are envisioned as being prepared as vaccines for these diseases.

Example I

In Vitro Culture of Parasites

The cloned line of *L. donovani* designated by the World Health Organization as MHOM/SD/62/1S-$C1_{2D}$ (SD) (Joshi, M. et al. 1995 *J Eukaryot Microbiol* 42:628-632) was used in all the experiments. Promastigotes and the axenic amastigotes were grown and harvested as described previously (Joshi, M. et al. 1993 *Mol Biochem Parasitol* 58:345-354). Wherever needed the parasites were counted visually under the microscope (ECLIPSE TE2000-U; Nikon corporation, Tokyo, Japan). In the experiments Student's t-test was used to determine the significance.

Construction of DNA for Targeted Gene Deletion

For *L. donovani* centrin gene knockout, nearly two thirds of the open reading frame (orf) from the 5' end (323/447 bp) was replaced with the orf of the selectable marker gene comprising either the hyg gene or neo gene. These genes were flanked at the 5' end by the 1198 bp upstream region of the LdCEN gene and at the 3' end by the 124 bp 3' region of the LdCEN orf followed by 716 bp of its downstream region. (A) The 5'UTR of LdCEN was amplified by PCR using a cosmid clone containing the LdCEN gene as template (Selvapandiyan, A. et al. 2001 *J Biol. Chem.* 276:43253-43261) and the following forward (P1) and reverse (P2) primers. P1: 5'-GGG ATC CTT ATA GCC ACG GAT G-3' (SEQ ID NO: 7) contains a BamHI restriction site (bold). P2: 5'-GGG TCG ACC CAC AAA AAG AAA TTG-3' (SEQ ID NO: 8) contains a SalI restriction site (bold). The resulting PCR product was cloned directly at the T/A cloning site of pCRII-TOPO cloning vector (Invitrogen Co.). The recombinant plasmid having the insert with the SalI end towards Sp6 promoter was cut with SpeI and KpnI and used in the next step. (B) The 3'UTR of LdCEN was PCR amplified using the cosmid clone mentioned above as template and the following forward (P3) and reverse (P4) primers. P3: 5'-GAC TAG TAC TGC TGG GTG AGA ACC-3' (SEQ ID NO: 9) contains a SpeI restriction site (bold). P4: 5'-GGG TAC CTA TTT ATC GCC TGC TCG G-3' (SEQ ID NO: 10) contains a KpnI restriction site (bold). The PCR product was restricted with SalI and KpnI and ligated at the same sites of the cut plasmid product of step A. The resulting recombinant plasmid was cut with SalI and SpeI and used in step C. (C) The selectable marker sequence hyg was amplified using plasmid pX63-HYG (Cruz, A. et al. 1991 *PNAS USA* 88:7170-7174) as template and forward (P5) and reverse (P6) primers. The neo gene was amplified using plasmid pKSNEO (Zhang, W. W. et al. 1996 *Mol Biochem Parasitol* 78:79-90) as template and forward (P7) and reverse (P8) primers. To ensure translation of these marker genes, nucleotides −16-+12 of 3'-nucleotidase/nuclease (3'NT/Nu) gene including the translation initiation site 'ATG' (Debrabant, A. et al. 2000 *J Biol Chem* 275:16366-16372; Debrabant, A. et al. 1995 *Mol Biochem Parasitol* 71:51-63) was added upstream of hyg and neo genes (M-seq; FIG. 1) during PCR amplification. This was based on our earlier experience of successful gene targeting to eliminate 3'NT/Nu gene. P5: 5'-G GTC GAC GCTACGGCAGACATGGCTCGAGCTCTG atg aaa aag cct gaa ctc-3' (SEQ ID NO: 11) contains sequentially a SalI restriction site (bold), 3'NT/Nu sequence as mentioned earlier (single underlined) and 18 nucleotide hyg sequence from beginning of orf (lower case). P6: 5'-GGA CTA GTC TAT TCC TTT GCC CTC G-3' (SEQ ID NO: 12) has a SpeI restriction site (bold) followed by 3' end sequence of hyg gene. P7: 5'-G GTC GAC GCTACGGCAGACATGGCTCGAGCTCTG atg att gaa caa gat gga-3' (SEQ ID NO: 13) is similar to primer P5 except that at its end instead of hyg sequence, it had 18 nucleotides neo sequence from beginning of orf (lower case). P8: 5'-GAC TAG TCA GAA GAA CTC GTC AAG-3' (SEQ ID NO: 14) has a SpeI restriction site (bold) followed by 3' end sequence of neo gene. Both the PCR amplified hyg and neo fragments were cut with SalI and SpeI restriction enzymes and the fragments were ligated at the cut plasmid obtained at step B. The authenticity of each of the constructs and the fidelity of the PCR amplified fragments were verified by nucleotide sequencing. The resulted hyg and neo recombinant plasmids were cut with BamHI and KpnI and the fragments of either hyg or neo flanked with the UTR sequences of LdCEN were individually used for transfection to disrupt LdCEN gene in *L. donovani.*

Transfection and Selection of LdCEN Null Mutant

Mid-log phase promastigotes ($2-4\times10^7$ cells/ml) were harvested by centrifugation at 3000 g for 10 min at 4° C. Cell pellets were washed in ice-cold PBS and electroporated with the DNA using conditions as described previously (Selvapandiyan, A. et al. 2001 *J Biol Chem.* 276:43253-43261). For clonal selection in general, the transfected promastigotes were incubated overnight in 5 ml *Leishmania* growth medium (Joshi, M. et al. 1995 *J Eukaryot Microbiol* 42:628-632). The following day the pellet of the culture was resuspended in 200 μl of the promastigote growth medium, syringe disrupted with 28G needle and plated on 1% agar plate containing the same growth medium supplemented with 4 μg/ml Biopterin (Calbiochem) from stock 200 μg/ml in 10 mM NaOH and respective antibiotic/s. The antibiotic unless otherwise mentioned G418 (Geneticin; BRL) was present at 40 μg/ml in plates and 20 μg/ml in liquid culture and corresponding concentrations of hygromycin B (Sigma) were 80 and 40 μg/ml respectively.

Transfection with construct #1 (FIG. 1) was performed as described above and finally plated on semi-solid plate containing hygromycin B. Clones isolated from the plates were subsequently expanded in liquid medium containing hygromycin B. Genomic DNA isolated from these cloned parasites was used in PCR and Southern blot analyses to confirm the loss of one allele of centrin. Such a cell line in which one allele of the centrin gene was substituted by the hyg gene was subjected to the next round of transfection using Construct #2 and clones were selected on the plate in the presence of both hygromycin B and G418 antibiotics. The clones were analyzed for the complete knockout of centrin, and the presence of both hyg and neo genes using PCR, Southern and Western blot analyses. The knockout clone was then propagated and used in subsequent experiments.

Southern and Western Blot Analyses

Isolation and Southern analysis of genomic DNA from *L. donovani* were performed as described previously (Selvapandiyan, A. et al. 2001 *J Biol Chem.* 276:43253-43261). Extraction of protein from the parasite and analysis by Western blot were also conducted as described previously (Selvapandiyan, A. et al. 2001 *J Biol Chem.* 276:43253-43261).

Light and 4'6-diamidino-2-phenylindole (DAPI)-Fluorescence Microscopy

For DAPI-fluorescence the parasites grown at different time points were washed once with 1×PBS and treated with tryphan blue. The cells were then air dried on the microscopic slide mounted in Vectashield containing 4'6-diamidino-2-phenylindole (DAPI)(Vector Laboratories, Inc.) to stain both nucleus and kinetoplast. Cells were examined for fluorescence under the ECLIPSE TE2000-U microscope (Nikon corporation, Tokyo, Japan) with epifluorescence and images captured with a digital camera (C4742-95), Hamamatsu Photonics K.K., Japan and processed with Open Lab software (Improvision, Inc.). Densely fluorescing kinetoplasts, observed in the viable cells (cells non stained with tryphan blue) were counted visually. For indirect immunofluorescence studies, 200 µl of cultured cells were harvested and mounted on slides using a Cytospin3 (Shandon, Pittsburgh Pa.). The preparation was fixed in −20° C. methanol for 10 min, blocked (10% goat serum, 5% glycerol, 0.1% NP40 in PBS) for 30 min and incubated with 1:2000 anti-centrin (20H5 ascites fluid) for 30 min. The preparation was then washed thoroughly with PBS, incubated in FITC conjugated secondary antibody for 30 min, washed again and stained for DNA using DAPI.

Electron Microscopy

Fixing of axenic amastigote cultures of wild type (+/+) and centrin deficient (−/−) parasites from 48 hr incubation point, embedding in epoxy resin, sectioning, staining and examining with an electron microscope were performed as described previously (Lee, N. et al. 2002 *Cell Death Differ* 9:53-64).

Flowcytometry

Axenic amastigotes from 24 and 48 hr cultures were collected, fixed in 70% ethanol, stained with 50 µg/ml propidium iodide (PI from Sigma) in PBS and analyzed as described previously (Selvapandiyan, A. et al. 2001 *J Biol Chem.* 276: 43253-43261). The data were analyzed using the Modfit Lt. Software, Verity Software House, Inc. (Topshan, Me.). For each sample 20,000 fluorescent events were measured. To analyze the plasma membrane integrity and PhiPhiLux (PPL) cleavage activity, promastigotes were inoculated at $1\times10^6$ cells/ml into axenic amastigote culture medium (Joshi, M. et al. 1993 *Mol Biochem Parasitol* 58:345-354) and samples of axenic amastigote cells collected at various times after inoculation. Fluorescence of the cells treated with both PI and PPL (Calbiochem, La Jolla, Calif., USA) was measured following published protocols (Lee, N. et al. 2002 *Cell Death Differ* 9:53-64). The data are expressed as percent of either PI or PPL positive parasites. All the above analyses were carried out using FACScan flow cytometer (Becton Dickinson Immunocytometry Systems, San Jose, Calif.) and CELLQuest software. For each sample 10,000 fluorescent events were measured.

TUNEL Assay

LdCEN$^{-/-}$ and wild type promastigotes were inoculated into axenic amastigote culture medium and allowed to grow for different periods of time, washed with PBS, fixed in 4% para-formaldehyde for 30 min, rinsed with PBS, permeabilized with 0.1% Triton X-100 in 0.1% sodium citrate for 2 min, rinsed with PBS and incubated with 50 µl per sample of TUNEL reaction mixture (Roche Diagnostics GmbH), containing FITC-labeled dUTP and terminal deoxynucleotidyl transferase, for 1 hr at 37° C. A negative control was included in each staining wherein only the labeling solution was added. To assess the nuclear morphology of the cells, the samples were stained, by mounting with Vectashield (Vector Laboratories, Inc.) containing DAPI. The specimens were then observed under a fluorescence microscope. DAPI fluorescent images were captured through a 364 nm wavelength filter and pseudocolored red to enhanced the contrast with the FITC image.

In Vitro Macrophage Infections

Human elutriated monocytes were resuspended at $1.8\times10^5$ cells/ml in RPMI medium containing macrophage colony stimulating factor (Debrabant, A. et al. 2002 *Int J Parasitol* 32:1423-1434), plated in 0.5 ml on eight chamber Lab-Tek tissue culture slides (Miles Laboratories) and incubated for 8 days for differentiation into macrophages. The differentiated macrophages were infected with stationary phase cultures of promastigotes (10:1, parasite to macrophage ratio) as described previously (Debrabant, A. et al. 2002 *Int J Parasitol* 32:1423-1434). After incubation for 5 hr at 37° C. in 5% $CO_2$, the free extracellular parasites were removed by repeated washings in RPMI, and the cultures were incubated in macrophage culture medium for maximum 240 h. At 5, 24, 48, 120 and 240 hr post infection (p.i.), the culture medium was removed from a sample of the culture slides, the slides were air-dried, fixed by immersion in absolute methanol for 5 min at room temperature and stained using Diff-Quick Stain set (Baxter Healthcare Corporation, Miami, Fla.). For each culture, a minimum of 300 macrophages were counted. Values are expressed either as percentage of macrophages that were infected by *Leishmania*, as the total number of amastigotes per 100 macrophage cells observed (infected plus noninfected) or as the mean number of parasites per infected macrophage.

Restoration of Centrin in LdCEN$^{-/-}$ Parasites

In order to restore centrin in the LdCEN$^{-/-}$ parasites, LdCEN orf was first PCR amplified using a LdCEN containing plasmid (Selvapandiyan, A. et al. 2001 *J Biol Chem.* 276:43253-43261) as template and the following forward (P9) and reverse (P10) primers. P9: 5'-GGG ATC CAT GGC TGC GCT GAC GGA T-3' (SEQ ID NO: 15) contains a BamHI restriction site (bold). P10: 5'-GGG ATC C CTACGCGTAGTCCGGCACGTCGTACGGGTAct ttc cac gca tgt gca g-3' (SEQ ID NO: 16) contains sequentially a BamHI restriction site, a sequence for an haemagglutinin tag (underlined) and 18 nucleotides of 3'-end of the LdCEN gene sequence (lower case). The amplified product was initially cloned at the T/A cloning site of pCRII-TOPO cloning vector (Invitrogen Co.). The fidelity of the cloned sequence was verified by nucleotide sequencing. The BamHI insert was subsequently cloned at the same cite of pXG-PHLEO vector (Engel, M. L. I et al. 2001 *Nucleic Acids Res* 29:725-731) and the recombinant plasmid, pXG-PHLEO-LdCEN, was transfected into the LdCEN$^{-/-}$ promastigotes as described previously (Selvapandiyan, A. et al. 2001 *J Biol Chem.* 276:43253-43261). Transfected promastigotes were selected with minimal doses of Phleomycin (Sigma) (10 μg/ml). In our experience, expression of protein through an episome is enhanced by increasing the concentration of selection drug in the medium. Hence, the selected promastigotes after each culture cycle were grown in gradually increasing Phleomycin levels up to 150 μg/ml. Parasites grown in the presence of 150 μg/ml of drug were used in subsequent experiments.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. An attenuated strain of *Leishmania* from the group consisting of *Leishmania donovani, Leishmania infantum, Leishmania chagasi, Leishmania major, Leishmania tropica, Leishmania aethiopica, Leishmania braziliensis, Leishmania mexicana*, and *Leishmania amazonensis*, wherein both wild-type copies of the single copy gene encoding centrin have been deleted to provide a strain incapable of expressing native centrin protein and having a reduced ability to infect or survive in macrophages in comparison to wild-type strain.

2. The strain of claim 1, wherein said deletion of at least one wild-type copy of the single copy gene leaves a gap into which is inserted a first marker gene.

3. The strain of claim 1 wherein said first marker gene encodes antibiotic resistance.

4. The strain of claim 3, in which said first marker gene encodes antibiotic resistance to a first antibiotic, and wherein said deletion of the other wild-type copy of the single copy gene leaves a gap into which is inserted a second marker gene, and wherein said second marker gene encodes antibiotic resistance to a second antibiotic.

5. An immunogenic composition comprising the attenuated strain of claim 1.

6. A method of generating an immune response in a host comprising administering thereto an immunoeffective amount of the immunogenic composition of claim 5.

* * * * *